(12) United States Patent
Lee et al.

(10) Patent No.: US 9,891,784 B2
(45) Date of Patent: Feb. 13, 2018

(54) APPARATUS AND METHOD OF DISPLAYING MEDICAL IMAGE

(71) Applicant: SAMSUNG MEDISON CO., LTD., Hongcheon-gun (KR)

(72) Inventors: Jin-yong Lee, Hongcheon-gun (KR); Joo-hyun Song, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 14/993,433

(22) Filed: Jan. 12, 2016

(65) Prior Publication Data

US 2016/0202875 A1    Jul. 14, 2016

(30) Foreign Application Priority Data

Jan. 12, 2015    (KR) .......................... 10-2015-0004452

(51) Int. Cl.
*G06F 3/0481*    (2013.01)
*A61B 8/00*    (2006.01)
(Continued)

(52) U.S. Cl.
CPC .......... *G06F 3/04815* (2013.01); *A61B 8/463* (2013.01); *A61B 8/465* (2013.01); *A61B 8/466* (2013.01); *A61B 8/469* (2013.01); *A61B 8/483* (2013.01); *A61B 8/5215* (2013.01); *G06F 3/04845* (2013.01); *G06F 19/3406* (2013.01); *G06T 15/08* (2013.01); *G06T 19/00* (2013.01); *G06T 19/20* (2013.01); *G06T 2210/41* (2013.01); *G06T 2219/008* (2013.01);
(Continued)

(58) Field of Classification Search
CPC ............. G06F 3/04815; G06F 3/04845; G06F 19/3406; A61B 8/463; A61B 8/465; A61B 8/469; A61B 8/485; A61B 8/5215; G06T 15/08
USPC ....................................................... 345/419
See application file for complete search history.

(56) References Cited

U.S. PATENT DOCUMENTS

| 6,733,458 B1 * | 5/2004 | Steins ................. A61B 8/0833 600/461 |
| 8,617,075 B2 | 12/2013 | Tsujita et al. |
| 2007/0279436 A1 * | 12/2007 | Ng .......................... G06T 19/00 345/624 |

(Continued)

FOREIGN PATENT DOCUMENTS

| EP | 2208467 A1 | 7/2010 |
| KR | 10-1014559 B1 | 2/2011 |

(Continued)

OTHER PUBLICATIONS

Communication dated Jun. 9, 2016, issued by the European Patent Office in counterpart European Application No. 15177325.6.

*Primary Examiner* — Barry Drennan
*Assistant Examiner* — Terrell Robinson
(74) *Attorney, Agent, or Firm* — Sughrue Mion, PLLC

(57) ABSTRACT

A method of displaying a medical image includes displaying a first image that is generated by rendering volume data of an object in a first direction, displaying on the first image a viewer tool for generating a second image, wherein the viewer tool indicates a section of the object, generating the second image by rendering sub-volume data included in the volume data in a second direction which is different from the first direction and indicated by the viewer tool, and displaying at least a part of the second image.

21 Claims, 24 Drawing Sheets

(51) Int. Cl.
    *G06F 3/0484*     (2013.01)
    *G06F 19/00*     (2011.01)
    *G06T 15/08*     (2011.01)
    *G06T 19/20*     (2011.01)
    *A61B 8/08*     (2006.01)
    *G06T 19/00*     (2011.01)

(52) U.S. Cl.
    CPC ................ *G06T 2219/2016* (2013.01); *G06T 2219/2021* (2013.01)

(56) References Cited

U.S. PATENT DOCUMENTS

| | | |
|---|---|---|
| 2010/0113931 A1 | 5/2010 | Lee |
| 2011/0235066 A1* | 9/2011 | Sakuragi ............... G06T 7/0022 358/1.6 |
| 2011/0282207 A1 | 11/2011 | Hashimoto |
| 2012/0113111 A1 | 5/2012 | Shiki et al. |
| 2012/0314842 A1* | 12/2012 | Kargar ................... A61B 6/107 378/86 |
| 2013/0195323 A1* | 8/2013 | Liu ....................... G06T 7/0083 382/128 |
| 2013/0328874 A1 | 12/2013 | Smith-Casem et al. |
| 2014/0003693 A1 | 1/2014 | Lee et al. |

FOREIGN PATENT DOCUMENTS

| | | |
|---|---|---|
| KR | 10-2011-0124037 A | 11/2011 |
| KR | 10-1126222 B1 | 3/2012 |
| KR | 10-2014-0002998 A | 1/2014 |
| KR | 10-2014-0038777 A | 3/2014 |

\* cited by examiner

APPARATUS AND METHOD OF DISPLAYING MEDICAL IMAGE

CROSS-REFERENCE TO RELATED APPLICATION

This application claims the benefit of Korean Patent Application No. 10-2015-0004452, filed on Jan. 12, 2015, in the Korean Intellectual Property Office, the disclosure of which is incorporated herein in its entirety by reference.

BACKGROUND

1. Field

One or more exemplary embodiments relate to an apparatus and method of displaying a medical image, and more particularly, to an apparatus and method of displaying a three-dimensional medical image that is generated by rendering volume data of an object.

2. Description of the Related Art

An ultrasound system having properties of being non-invasive and non-destructive has been widely used in a medical field to obtain information about the inside of an object. Since the ultrasound system may provide a doctor with a high resolution image of the inside of an object without a surgical operation for directly incising the object to observe the inside of the object, the ultrasound system is very important in the medical field.

In general, the ultrasound system in a state in which a probe is in contact with a surface of the object transmits an ultrasound signal to the object and receives an ultrasound signal (hereinafter, referred to as an echo signal) reflected from the object. The ultrasound system generates an ultrasound image of the object based on the echo signal received through the probe and displays a generated ultrasound signal through a display.

For example, the ultrasound system may generate and display a brightness mode (B Mode) image that represents the strength of the echo signal reflected from the object in terms of brightness or a Doppler mode (D Mode) image that represents a Doppler component extracted from the echo mode in terms of color or waveform. Also, the ultrasound system may generate volume data based on the echo signal reflected from the object and may generate and display a three-dimensional ultrasound image by rendering the volume data.

In providing a three-dimensional ultrasound image, a general ultrasound system generates and displays only three-dimensional ultrasound images of predetermined cross-sections. Accordingly, since a user receives only the three-dimensional ultrasound images rendered in a predetermined direction with regard to the predetermined cross-sections, it is difficult to precisely observe a desired portion in detail.

SUMMARY

One or more exemplary embodiments include an apparatus and method of displaying a medical image that is generated by rendering volume data in a plurality of directions to observe the inside of an object at various angles.

Additional aspects will be set forth in part in the description which follows and, in part, will be apparent from the description, or may be learned by practice of the presented exemplary embodiments.

According to one or more exemplary embodiments, a method of displaying a medical image includes displaying a first image that is generated by rendering volume data of an object in a first direction, displaying on the first image a viewer tool for generating a second image, wherein the viewer tool indicates a section of the object, generating the second image by rendering sub-volume data included in the volume data in a second direction which is different from the first direction and indicated by the viewer tool, and displaying at least a part of the second image.

The generating of the second image may include determining the second direction based on at least one of a position, an angle, and a shape of the viewer tool displayed on the first image.

The viewer tool may include direction information indicating the second direction, and the generating of the second image may include determining the section of the object based on at least one of a position, an angle, and a shape of the viewer tool displayed on the first image, and determining which one of two directions perpendicular to the section is the second direction, based on the direction information.

The displaying of the viewer tool may include displaying viewing angle information indicating a range of the object represented by the second image that is generated based on the viewer tool, and the generating of the second image may include determining the second direction based on at least one of a position, an angle, and a shape of the viewer tool displayed on the first image, and generating the second image by rendering sub-volume data included in the volume data in the second direction indicated by the viewer tool based on the viewing angle information.

The viewer tool may include direction information indicating which one of two directions that are perpendicular to the section of the object indicated by the viewer tool is the second direction.

The first image may be generated by rendering in the first direction one of two pieces of sub-volume data obtained by dividing the volume data based on a first section of the object, and the second image may be generated by rendering in the second direction one of two pieces of sub-volume data obtained by dividing the volume data based on a second section of the object, in which the second section crosses the first section.

The first image may be generated by rendering in the first direction one of two pieces of sub-volume data obtained by dividing the volume data based on a first section of the object, and the second image may be generated by rendering in the second direction the other one of the two pieces of sub-volume data obtained by dividing the volume data based on the first section of the object, in which the second direction is opposite to the first direction.

The second image may be displayed on the viewer tool.

The second image may be generated by rendering the sub-volume data with a rendering parameter that is different from a rendering parameter applied to the first image.

The method may further include enlarging or contracting the second image based on a user input.

The method may further include changing a display mode based on a user input such that the viewer tool and the second image are not displayed on the first image.

The method may further include changing at least one of a position, an angle, and a shape of the viewer tool based on a user input, generating a third image by rendering the volume data based on the change of the at least one of the position, the angle, a size, and the shape of the viewer tool, and displaying the third image instead of the second image.

According to one or more exemplary embodiments, an apparatus for displaying a medical image includes a volume data acquirer acquiring volume data of an object, an image processor generating a first image by rendering the volume data in a first direction, a display displaying the first image and displaying on the first image a viewer tool for generating a second image, the viewer tool indicating a section of the object, and a controller determining a second direction based on the viewer tool, in which the image processor generates the second image by rendering sub-volume data included in the volume data in a second direction which is different from the first direction and indicated by the viewer tool, and the display displays at least a part of the second image.

The controller may determine the second direction based on at least one of a position, an angle, and a shape of the viewer tool displayed on the first image.

The viewer tool may include direction information indicating the second direction, and the controller may determine the section of the object based on at least one of a position, an angle, and a shape of the viewer tool displayed on the first image; and determine which one of two directions perpendicular to the section is the second direction, based on the direction information.

The display may further display viewing angle information indicating a range of the object represented by the second image that is generated based on the viewer tool, the controller may determine the second direction based on at least one of a position, an angle, and a shape of the viewer tool displayed on the first image, and the image processor may generate the second image by rendering sub-volume data included in the volume data in the second direction indicated by the viewer tool based on the viewing angle information.

The viewer tool may include direction information indicating which one of two directions that are perpendicular to the section of the object indicated by the viewer tool is the second direction.

The first image may be generated by rendering in the first direction one of two pieces of sub-volume data obtained by dividing the volume data based on a first section of the object, and the second image may be generated by rendering in the second direction one of two pieces of sub-volume data obtained by dividing the volume data based on a second section of the object, in which the second section crosses the first section.

The first image may be generated by rendering in the first direction one of two pieces of sub-volume data obtained by dividing the volume data based on a first section of the object, and the second image may be generated by rendering in the second direction the other one of the two pieces of sub-volume data obtained by dividing the volume data based on the first section of the object, in which the second direction being opposite to the first direction.

The second image may be displayed on the viewer tool.

The second image may be generated by rendering the sub-volume data with a rendering parameter that is different from a rendering parameter applied to the first image.

The apparatus may further include a user input unit that receives a user input, in which the display displays the second image which is enlarged or contracted based on the user input.

The apparatus may further include a user input unit that receives a user input, in which the display changes a display mode based on the user input such that the viewer tool and the second image are not displayed on the first image.

The apparatus may further include a user input unit that receives a user input, in which the display may display the viewer tool of which at least one of a position, an angle, and a shape is changed based on the user input, the image processor may generate a third image by rendering the volume data based on the viewer tool of which at least one of the position, the angle, a size, and the shape of the viewer tool is changed, and the display may display the third image instead of the second image.

According to one or more exemplary embodiments, a non-transitory computer-readable storage medium having stored thereon a program, which when executed by a computer, performs a method for display a medical image, in which the method may include displaying a first image that is generated by rendering volume data of an object in a first direction, displaying on the first image a viewer tool for generating a second image that is rendered in a second direction different from the first direction, wherein the viewer tool indicates a section of the object, generating the second image by rendering sub-volume data included in the volume data in the second direction indicated by the viewer tool, and displaying at least a part of the second image.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
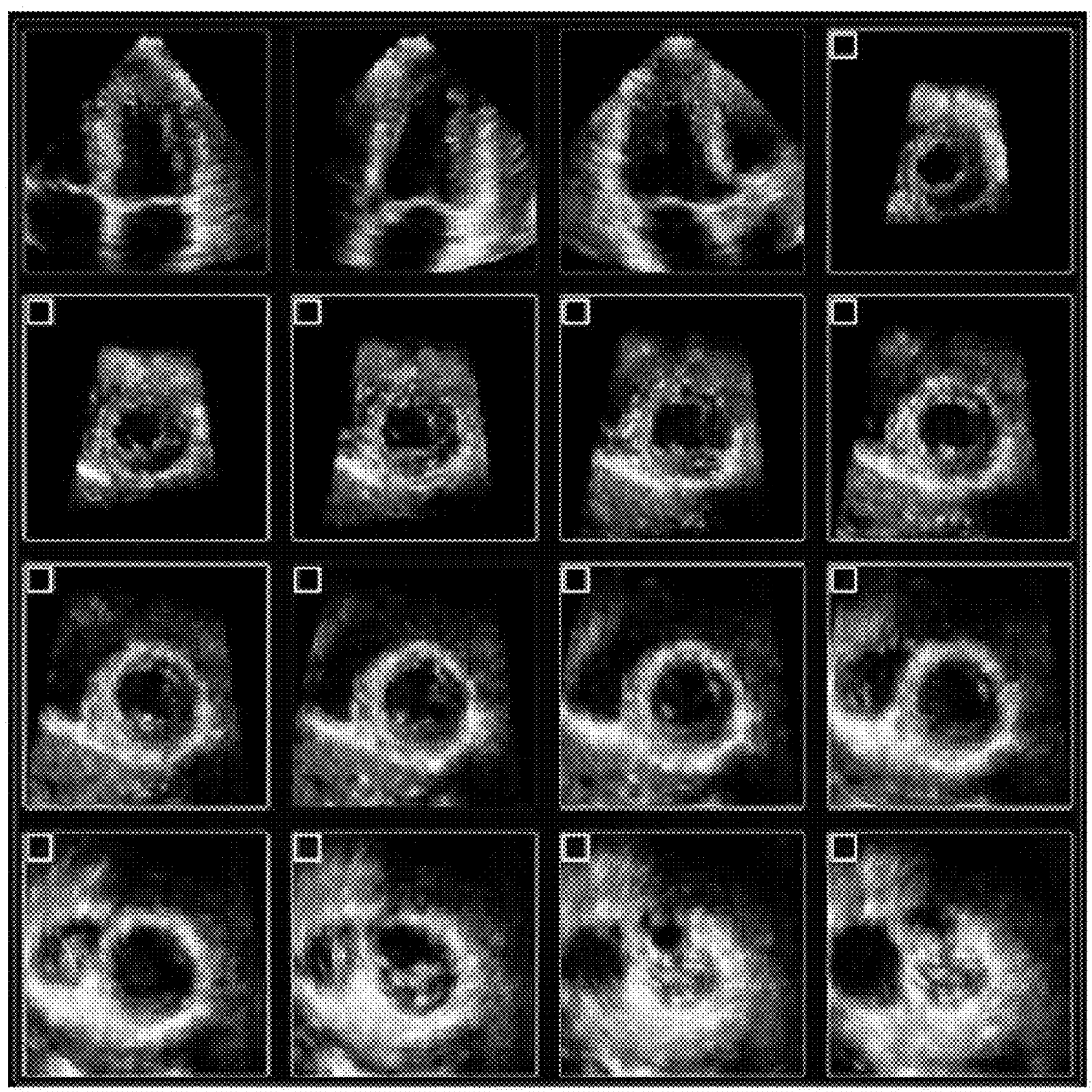
FIG. 1 illustrates an example of a screen showing three-dimensional ultrasound images in a general ultrasound system.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The present invention will now be described more fully with reference to the accompanying drawings, in which exemplary embodiments of the invention are shown. Throughout the drawings, like reference numerals denote like elements. In the following description, when detailed descriptions about related well-known functions or structures are determined to make the gist of the present invention unclear, the detailed descriptions will be omitted herein.

When a part may "include" a certain constituent element, unless specified otherwise, it may not be construed to exclude another constituent element but may be construed to further include other constituent elements. Terms such as "~portion", "~unit", "~module", and "~block" stated in the specification may signify a unit to process at least one function or operation and the unit may be embodied by hardware, software, or a combination of hardware and software. Also, as a computer software command to embody the present invention, hardware, software, or a combination of hardware and software may be used instead of a programmed processor/controller. Accordingly, the present invention is not limited by a specific combination of hardware and software.

In the present specification, when a constituent element "connects" or is "connected" to another constituent element, the constituent element contacts or is connected to the other constituent element directly or through at least one of other constituent elements. Conversely, when a constituent element is described to "directly connect" or to be "directly connected" to another constituent element, the constituent element should be construed to be directly connected to another constituent element without any other constituent element interposed therebetween.

In the present specification, an "object" may be a living thing or a non-living thing displayed on an image. Also, the object may be a part of a human and may include organs such as the liver, the heart, the womb, the brain, a breast, the abdomen, etc., or a fetus. Also, the object may include any one section of a human body.

Also, in the present specification, a "user" may be a medical expert including a doctor, a nurse, a clinical pathologist, a sonographer, or a medical imaging expert, but the present invention is not limited thereto.

Also, in the present specification, a "medical image" may include all images for diagnosis and treatment of a disease by which sectional and volume data of a part of a human body are restored from signals projected to the part, for example, a computed tomography (CT) image, a magnetic resonance imaging (MRI) image, or a positron emission tomography (PET), in addition to an ultrasound image. Also, the "medical image" may include all of two-dimensional (2D) image of a section of an object, a three-dimensional (3D) image of a space of the object, and a stereo image which enables a viewer watching an image to feel a sense of depth. The present inventive concept is described below in detail with reference to the accompanying drawings.

FIG. 1 illustrates an example of a screen showing 3D ultrasound images in a general ultrasound system.

As illustrated in FIG. 1, a general ultrasound system provides 3D images that are generated by rendering volume of an object based on predetermined sections of the object. Accordingly, image about the predetermined sections provided by the general ultrasound system may not images about a portion that a user wants to observe of the object.

Also, the general ultrasound system provides 3D ultrasound images that are generated by rendering volume data in a predetermined direction. For example, the general ultrasound system provides only 3D ultrasound images that are rendered in a direction in which the inside of a human body is viewed from the outside. Accordingly, the user who received the 3D ultrasound images from general ultrasound system has difficulty precisely observing the portion to observe at various angles.

Accordingly, various exemplary embodiments of the present inventive concept provide an apparatus and method of displaying a medical image which provides a user interface (UI) to set a direction in which volume data is rendered so that the user may observe the inside of the object at various angles.

Figure 2:
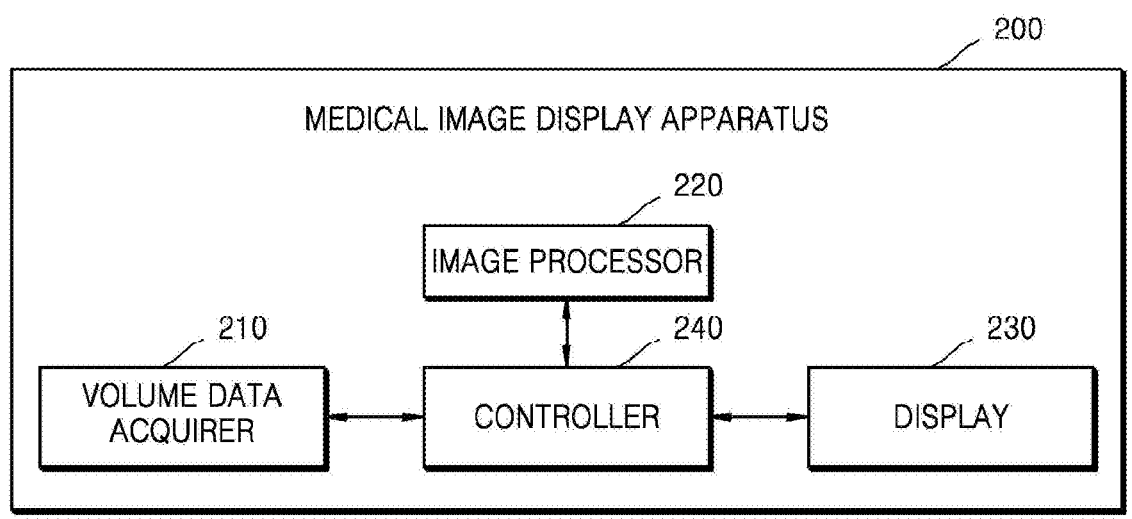
FIG. 2 is a block diagram of an apparatus for displaying a medical image according to an exemplary embodiment.

FIG. 2 is a block diagram of the medical image display apparatus 200 according to an exemplary embodiment.

The medical image display apparatus 200 according to the present exemplary embodiment may be embodied not only in a card type but also in a mobile type, as an apparatus for generating and displaying by rendering volume data. The medical image display apparatus 200 may be an apparatus developed for a medical use, but not limited thereto, and may include all apparatuses that may process and display an image. For example, the medical image display apparatus 200 may include a fax viewer such as a Picture Archiving and Communication System (PACS) viewer, hand-carried cardiac ultrasound (HCU) equipment, smartphones, laptop computers, personal digital assistants (PDAs), tablet PC, etc.

The medical image display apparatus 200 according to the present exemplary embodiment may include a volume data acquirer 210, an image processor 220, a display 230, and a controller 240. The medical image display apparatus 200 in FIG. 2 is illustrated to include only elements related to the present exemplary embodiment. Accordingly, one of ordinary skill in the art would understand that other common elements than the elements illustrated in FIG. 2 may be further included.

The volume data acquirer 210 may acquire volume data of the object.

The term "volume data" signifies data including information, for example, a position, a color, a density, etc., about a plurality of voxels forming a 3D space. A voxel may be a unit for defining a point in a 3D space. The volume data of the object may include space information about the space of an object or clinical information such as an anatomical shape of a tissue or an organ included of the object. For example, the volume data of the object may be ultrasound data acquired from an ultrasound echo signal reflected from the object in response to the ultrasound signal transmitted to the object.

In an example, the volume data acquirer 210 may acquire volume data by forming volume data of the object by using the ultrasound data acquired by the object. In another example, the volume data acquirer 210 may acquire volume data from an external device or server. In another example, the volume data acquirer 210 may acquire volume data that is previously stored.

The image processor 220 may generate a first image by rendering the volume data in a first direction. The first image may be a 2D image or a 3D image.

The term "rendering" is technology to form and display a projection image of a 3D discretely sampled data set such as the volume data. For example, a method of rendering volume data includes a ray casting method in which a part of the object is detected by casting an imaginary light ray toward the object.

The expression "rendering the volume data in a predetermined direction" signifies generating a 3D image obtained by projecting the volume data in a predetermined direction. In other words, the expression "rendering the volume data in a predetermined direction" signifies generating an image of the object by using an imaginary camera that watches the object in a predetermined direction in an imaginary space where the object is located.

The first direction may be a direction that is preset as a default value or determined based on a user input in the medical image display apparatus 200.

Also, the image processor 220 may further generate a second image by rendering the volume data in a second direction that is determined through a viewer tool displayed through the display 230.

The image processor 220 may generate a plurality of images by rendering the volume data in different directions with respect to one section of the object.

For example, the image processor 220 may generate the first image by rendering in the first direction one of two pieces of sub-volume data obtained by dividing the volume data based on the first section of the object. The image processor 220 may generate the second image by rendering the other sub-volume data in the second direction that is the opposite direction to the first direction.

Alternatively, the image processor 220 may generate a plurality of images by rendering the volume data in different directions based on different sections of the object. For example, the image processor 220 may generate the first image by rendering in the first direction one of two pieces of sub-volume data obtained by dividing the volume data based on the first section of the object.

The image processor 220 may generate the second image by rendering the volume data based on a second section of the object shown by the viewer tool. The image processor 220 may generate the second image by rendering in the second direction one of two pieces of sub-volume data obtained by dividing the volume data based on the second section that crosses the first section.

The image processor 220 may generate the second image by using a rendering parameter that is different from a rendering parameter applied to the first image. The rendering parameter may include opacity, level of detail, brightness, and a rendering method. For example, the image processor 220 may generate the first and second images by rendering the volume data in different methods. Alternatively, the image processor 220 may render the volume data by using different brightness parameters so that an average brightness of the second image is brighter than the brightness of the first image.

Also, the image processor 220 may generate the second image, as if the user may receive an image reflected from a concave mirror or a convex mirror inserted into the inside of the object. The image processor 220 may provide various ways of distortion effects, by applying various filters to the second image generated by rendering the volume data. The distortion effect signifies giving a sense of refraction to an image by enlarging or contracting at least a part of the image, or moving the positions of pixels.

The display 230 displays a medical image generated by the medical image display apparatus 200. The display 230 may display not only the medical image generated by the medical image display apparatus 200 but also various pieces of information processed by a medical diagnosis apparatus 100 through a graphical user interface (GUI).

The display 230 may include at least one of a liquid crystal display, a thin film transistor-liquid crystal display, an organic light-emitting diode, a flexible display, a 3D display, and an electrophoretic display. The medical image display apparatus 200 may include two or more of the display 230 according to an embodiment shape of the medical image display apparatus 200.

The display 230 may display the first image generated by the image processor 220. The display 230 may display on the first image the viewer tool for generating the second image rendered in the second direction that is different from the first direction. The display 230 may display at least a part of the second image generated by the image processor 220 based on the viewer tool. For example, the display 230 may generate the first image by rendering the volume data in a direction from the outside of the object toward the inside of the object, and the second image by rendering the volume data in a direction from the inside of the object toward the outside of the object.

The display 230 according to the present exemplary embodiment may display on the first image the viewer tool for observing the object from a different viewpoint from the first image of the object. The image processor 220 may further generate the second image by rendering the volume data of the object in the second direction that is different from the first direction, based on the viewer tool displayed on the first image. The display 230 may show through the second image an inner portion of the object that is not displayed through the first image, by further displaying the second image.

According to the viewer tool according to an example embodiment, the user may variously set a viewpoint to observe the inside of the object. Accordingly, according to the present exemplary embodiment, the user may observe the inside of the object at various angles.

The viewer tool may include direction information indicating the second direction to render the volume data. For example, the medical image display apparatus 200 may indicate the direction information by using at least one of characters, signs, shapes, and colors. The viewer tool, which is displayed on the first image, may show the second section that crosses, is parallel to, or is the same as the first section that the first image represents. The second direction may be perpendicular to the second section. The medical image display apparatus 200 may generate the second image by rendering the volume data in a direction perpendicular to the second section of the object determined by the viewer tool. The direction information included in the viewer tool may indicate in which of two directions perpendicular to the second section the volume data is rendered.

The viewer tool may show a section of the object to determine two pieces of sub-volume data, by dividing the volume data. The medical image display apparatus 200 may determine which of the two pieces of sub-volume data determined based on the viewer tool is to be rendered, based on the direction information included in the viewer tool.

The display 230 may display at least a part of the second image generated by the image processor 220 based on the viewer tool. The medical image display apparatus 200 may select at least a partial area of the second image based on the position, size, and shape of the viewer tool on the first image. The display 230 of the medical image display apparatus 200 may display the selected partial area on a screen.

The display 230 may separately display the first image and the second image in different areas on the screen. Alternatively, the display 230 may display the first image and the second image in one area so that the second image is displayed overlapping the first image. For example, the display 230 may display the second image on the viewer tool.

Also, the display 230 may further display viewing angle information about a range of the object indicated by the second image generated based on the viewer tool. The image processor 220 may generate the second image by rendering the sub-volume data included in the volume data in the second direction indicated by the viewer angle, based on the viewing angle information.

The controller 240 controls an overall operation of the medical image display apparatus 200 and controls the volume data acquirer 210, the image processor 220, and the display 230 to display a medical image based on an operation state of the medical image display apparatus 200.

The controller 240 may determine the second direction to render the volume data based on the viewer tool. The controller 240 may determine the second direction based on at least one of the position, angle, and shape of the viewer toll displayed on the first image.

The controller 240 may determine one section of the object based on at least one of the position, angle, and shape of the viewer tool displayed on the first image. The controller 240 may determine one of two direction perpendicular to the section as the second direction, based on the direction information presented by the viewer tool.

Figure 3:
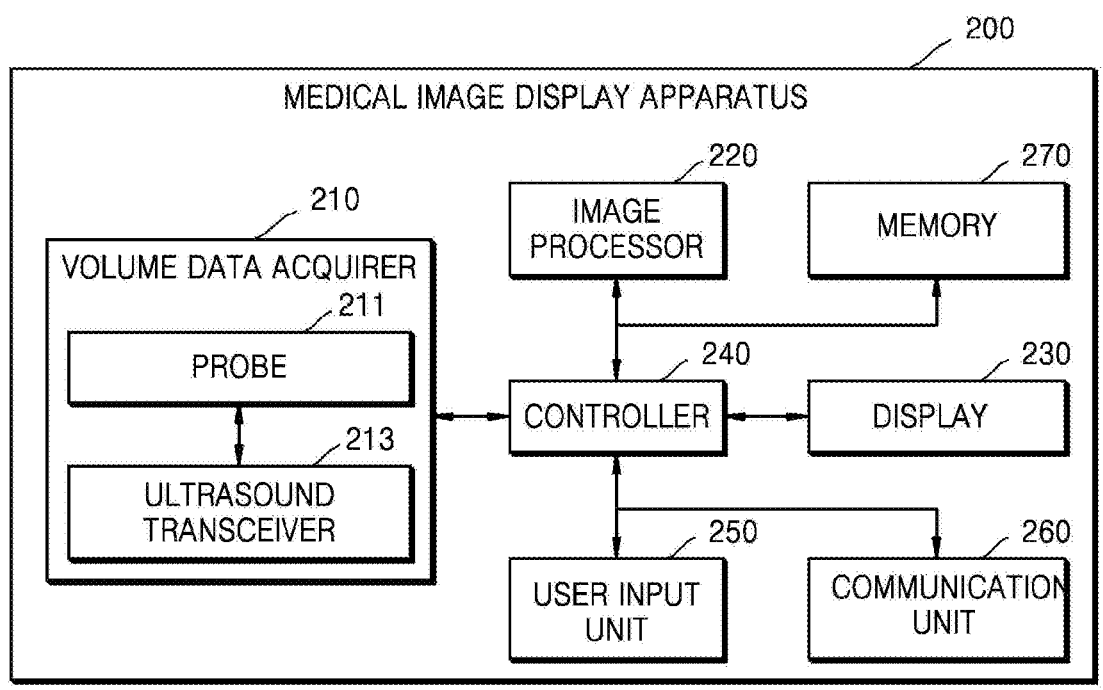
FIG. 3 is a detailed block diagram of an apparatus for displaying a medical image according to an exemplary embodiment.

Also, as illustrated in FIG. 3, the medical image display apparatus 200 according to the present exemplary embodiment may further include a user input unit 250, a communication unit 260, and a memory 270. Also, the volume data acquirer 210 may include a probe 211 and an ultrasound transceiver 213.

The user input unit 250 signifies a unit for receiving an input of data to control the medical image display apparatus 200. The user input unit 250 may receive a user input to adjust a medical image to be displayed through the medical image display apparatus 200. For example, the user input unit 250 may receive a user input to enlarge or contract a displayed image, a user input to change a display mode, a user input to change at least one of the position, angle, size, and shape of the viewer tool, and an user input to adjust a range of the object indicated by the second image generated based on the viewer tool. The user may change a position of an area to observe of the object or an angle to observe the inside of the object, by changing at least one of the position, angle, size, and shape of the viewer tool.

For example, the display 230 may enlarge or contract a displayed image, based on the use input received through the user input unit 250. The display 230 may display the second image that is enlarged or contracted based on the user input.

Alternatively, the display 230 may change the display mode based on the user input received through the user input unit 250. The display 230 may change the display mode to prevent the viewer tool and the second image from being displayed on the first image, based on the user input.

Alternatively, the display 230 may display the viewer tool of which at least one of the position, angle, size, and shape is changed based on the user input to the viewer tool. As at least one of the position, angle, size, and shape of the viewer tool is changed, the image processor 220 may change a section of the object that is a reference for generating the second image. Also, the image processor 220 may change the second direction for rendering the volume data to generate the second image, as at least one of the position, angle, size, and shape of the viewer tool. The image processor 220 may generate a third image by rendering the volume data based on the viewer tool in which at least one of the position, angle, size, and shape is changed. The third image may be displayed instead of the second image.

Also, the user input unit 250 may receive from the user display setting information to set a method of displaying medical images on the screen. The display setting information may include information about setting of the number of divided screens to display an image or the position or size of an area where the image is displayed. The display 230 may change a screen structure based on the display setting information received through the user input unit 250.

Also, the user input unit 250 may receive from the user the viewing angle information about the range of the object indicated by the second image generated based on the viewer tool. The display 230 may change a spatial area of the object indicated by the second image to increase or decrease based on the viewing angle information received through the user input unit 250.

The user input unit 250 may include a hardware structure such as a keypad, a touch panel, a touch screen, a trackball, a jog switch, etc., but not limited thereto. The user input unit 250 may further include various input devices such as an electrocardiogram measurement module, a respiration measurement module, a voice recognition sensor, a gesture recognition sensor, a fingerprint recognition sensor, an iris recognition sensor, a depth sensor, a distance sensor, etc.

The communication unit 260 is connected to a network 1030 in a wired or wireless manner and communicates with an external device or server. For example, the communication unit 260 may receive the volume data of the object from the external device or server, and transfer the received volume data to the volume data acquirer 210.

The memory 270 stores various pieces of information processed by the medical image display apparatus 200. For example, the memory 270 may store medical data related to a medical image or diagnosis of the object, or an algorithm or program performed in the medical image display apparatus 200.

The memory 270 may be embodied by various types of storage media such as flash memory, hard disk, EEPROM, etc. Also, the memory 270 may run a web storage or a cloud server that performs a storing function on the web. The memory 270 may store the volume data of the object, and transfers the stored volume data to the volume data acquirer 210.

The volume data acquirer 210 according to the present exemplary embodiment may transmit an ultrasound signal to the object and receive an ultrasound echo signal from the object, thereby acquiring the volume data.

As illustrated in FIG. 3, the volume data acquirer 210 may include the probe 211 and the ultrasound transceiver 213.

The probe 211 may transmit an ultrasound signal to the object according to a control signal transmitted by the ultrasound transceiver 213 and receive an ultrasound echo signal reflected from the object, thereby forming a receiving signal. The probe 211 may transmit the receiving signal to the ultrasound transceiver 213.

The ultrasound transceiver 213 supplies a driving signal to the probe 211 so that the probe 211 transmits an ultrasound signal to the object. Also, the ultrasound transceiver 213 forms ultrasound image data by using the receiving signal received from the probe 211.

The volume data acquirer 210 may form the volume data by combining the ultrasound image data about a plurality of sections of the object formed by the ultrasound transceiver 213.

Figure 4:
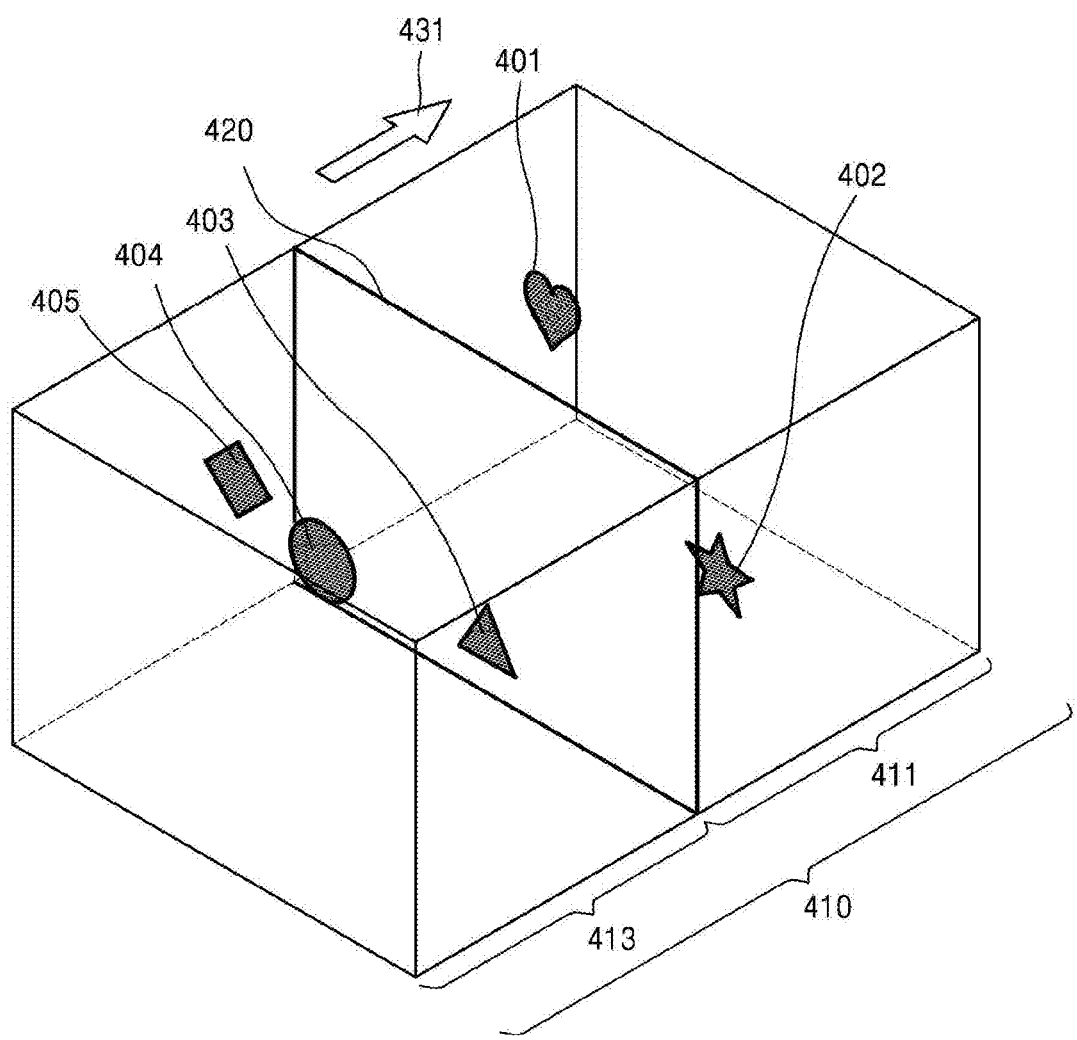
FIGS. 4 and 5 are views for explaining a method of generating a first image by rendering volume data in a first direction, according to an exemplary embodiment.
Figure 5:
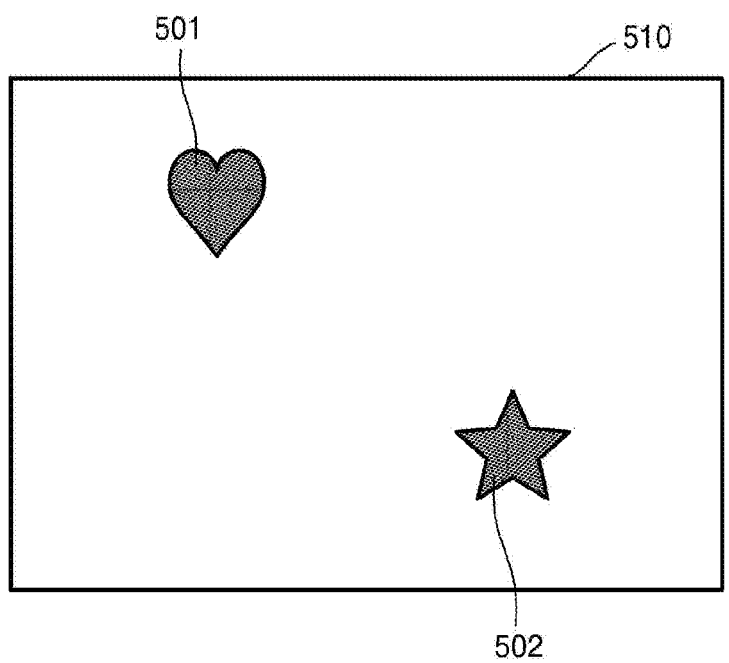

FIGS. 4 and 5 are views for explaining a method of generating the first image by rendering volume data in the first direction, according to an exemplary embodiment.

FIG. 4 illustrates volume data 410 of the object, and a case in which various tissues, for example, blood vessels, muscle, tumors, etc. are included in the volume data 410.

As illustrated in FIG. 4, according to the present exemplary embodiment, the medical image display apparatus 200 may generate a first image 510 of FIG. 5 by rendering the volume data 410 in a first direction indicated by an arrow 431.

The medical image display apparatus 200 may generate the first image 510 showing the inside of the object based on a first section 420. The medical image display apparatus 200 may determine two pieces of sub-volume data 411 and 413 by dividing the volume data 410 based on the first section 420 of the object.

The medical image display apparatus 200 may generate the first image 510 of FIG. 5 by rendering one of two pieces of the sub-volume data 411 and 413 in the first direction. The first direction may be perpendicular to the first section 420. The first image 510 of FIG. 5 includes images 501 and 502 indicating tissues 401 and 402 included in the sub-volume data 411.

The medical image display apparatus 200 according to the present exemplary embodiment may provide the viewer tool for setting a region of interest (ROI) so that the user may observe the ROI to observe at various angles.

FIGS. 6 to 10 are views for explaining a method of generating the second image by rendering the volume data in the second direction based on the viewer tool, according to an exemplary embodiment. The viewer tool may signify a user interface for setting a ROI.

Figure 6:
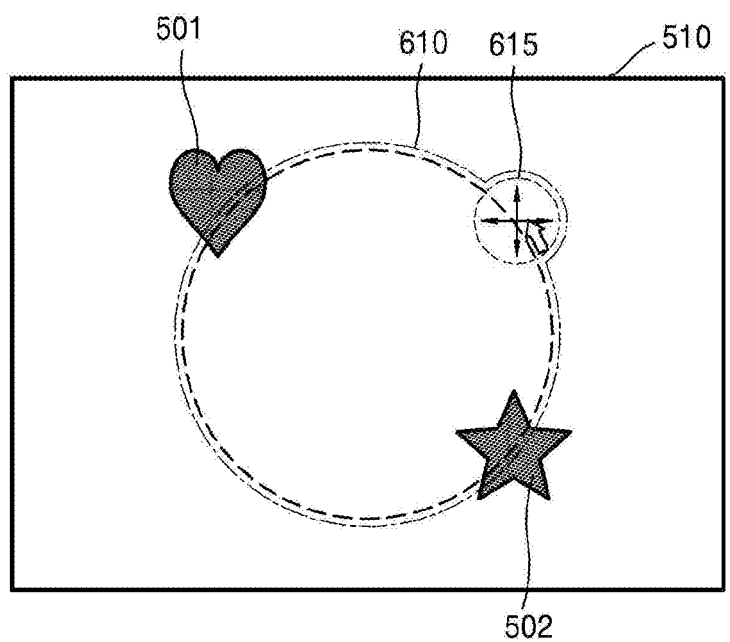
FIGS. 6 to 10 are views for explaining a method of generating a second image by rendering volume data in a second direction based on a viewer tool, according to an exemplary embodiment.

As illustrated in FIG. 6, the medical image display apparatus 200 may display a viewer tool 610 on the first image 510. The viewer tool 610 may include a viewer tool cursor 615 so that the user may set at least one of the position, size, and shape of the viewer tool 610. The user may adjust the at least one of the position, size, and shape of the viewer tool 610 by changing the position of the viewer tool cursor 615.

For example, the user may select a reference position to set the viewer tool 610 by locating the viewer tool cursor at a desired position on the first image 510 and selecting the position. The user may set the size and shape of the ROI by moving the viewer tool cursor 615 to another position from the reference position. The medical image display apparatus 200 may set the at least one of the position, size, and shape of the viewer tool 610 based on a user input to move the viewer tool cursor 615. When the ROI is set, the viewer tool 610 may display the position, size, and shape of the set ROI on the first image 510.

FIG. 6 illustrates an exemplary case in which the user sets the position, size, and shape of the viewer tool by using the viewer tool cursor 615. However, the present exemplary embodiment is not limited thereto, and the medical image display apparatus 200 may provide a viewer tool of a predetermined shape, and change the position, size, and shape of the viewer tool based on the user input.

Figure 7:
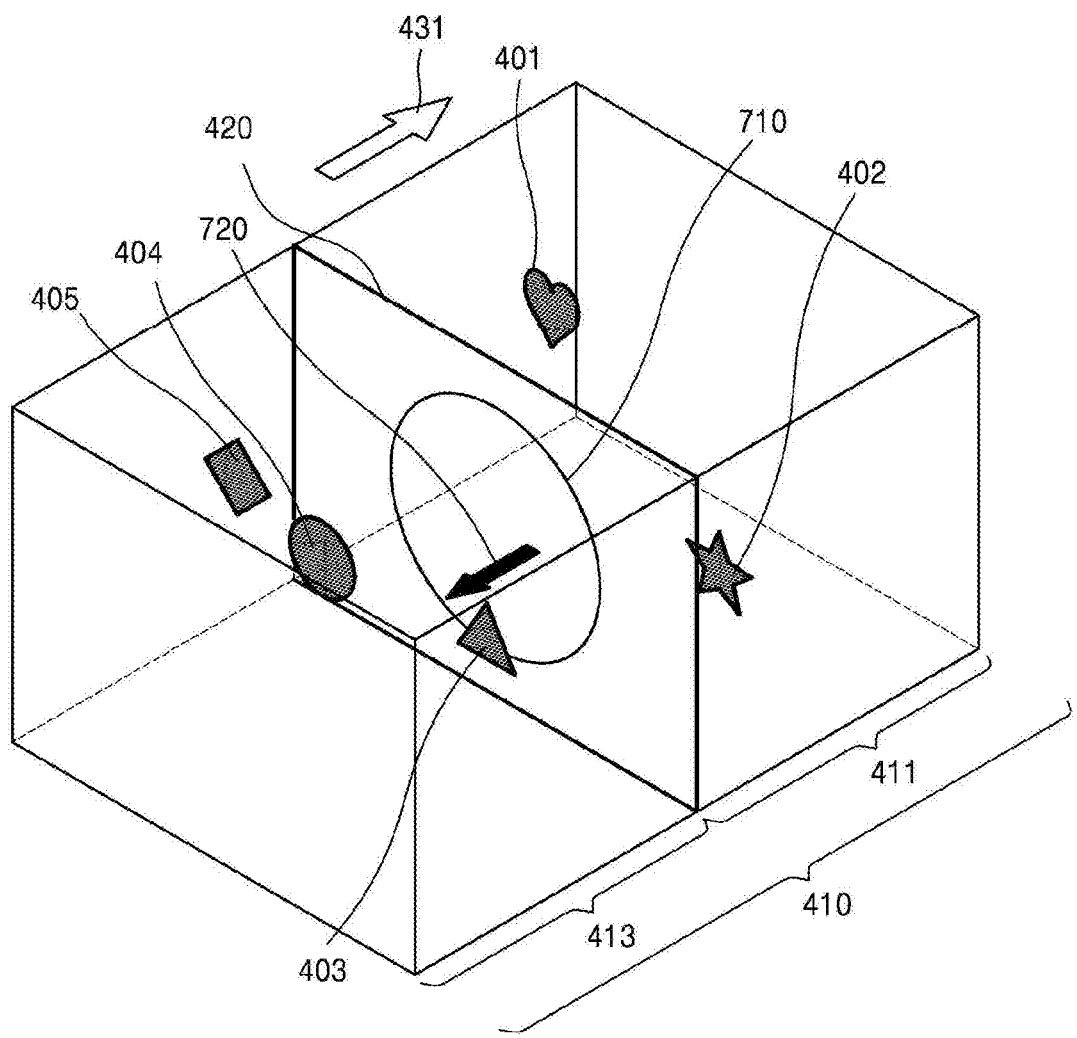

The medical image display apparatus 200 may determine the second direction to render the volume data based on the viewer tool 610 set on the first image 510. For example, as illustrated in FIG. 7, the medical image display apparatus 200 may determine a direction that is perpendicular to the first section 420 and opposite to the first direction indicated by the arrow 431, as the second direction. The second direction is indicated by an arrow 720.

The medical image display apparatus 200 may generate the second image by rendering the other one of the two sub-volume data 411 and 413 in the second direction. The medical image display apparatus 200 may generate the second image based on at least one of the position, angle, size, and shape of the viewer tool 610. For example, the medical image display apparatus 200 may generate the second image showing tissues 403 and 404 in the sub-volume data 413 corresponding to the position, size, angle, and shape of the viewer tool 610.

For example, the medical image display apparatus 200 may determine the second section of the object based on the viewer tool 610. The second section may be the same as or different from the first section that is used as a reference for generating the first image 510. The medical image display apparatus 200 may determine the second section of the object based on the position, angle, size, and shape of the viewer tool 610.

The medical image display apparatus 200 may divide the volume data into two sub-volume data based on the second section, and generate the second image by rendering one of the two sub-volume data in the second direction. For example, the second direction may be perpendicular to the second section, and may be a direction determined based on direction information included in the viewer tool 610.

The medical image display apparatus 200 may select at least a partial area of the second image on the first image 510, based on the position, size, and shape of the viewer tool 610. The medical image display apparatus 200 may display the selected partial area on the screen.

Figure 8:
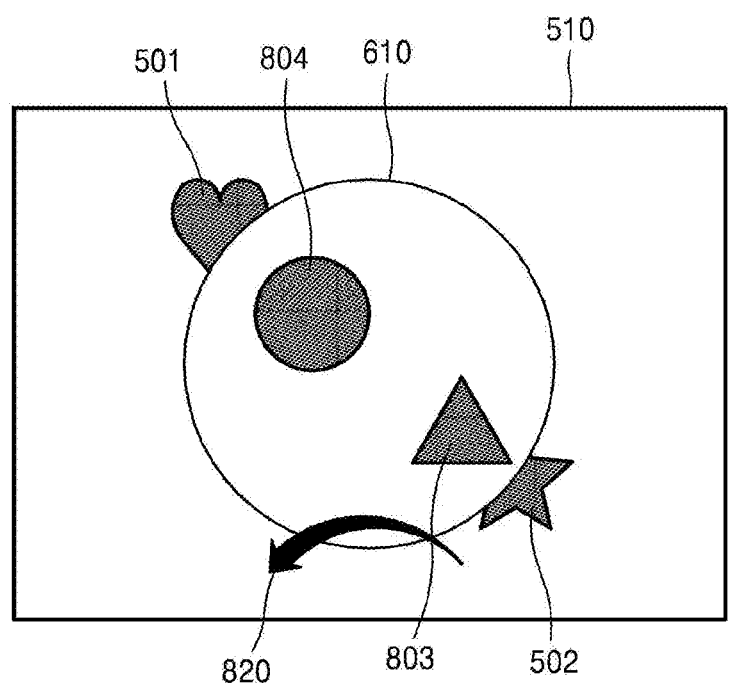

As illustrated in FIG. 7, according to the present exemplary embodiment, the medical image display apparatus 200 may generate the second image by rendering the volume data 410 in the second direction indicated by the arrow 720. As illustrated in FIG. 8, the second image may be displayed on the viewer tool 610. The second image of FIG. 8 includes images 803 and 804 that represent the tissues 403 and 404 included in the sub-volume data 413, corresponding to the position, size, and shape of the viewer tool 610.

FIGS. 7 and 8 illustrate an exemplary case in which the medical image display apparatus 200 generates the first and second images by rendering the volume data in different directions with respect to the same section. However, the present exemplary embodiment is not limited thereto and the medical image display apparatus 200 may generate the second image by rendering the volume data with respect to the section that is different from the first section. For example, as indicated by an arrow 820 in FIG. 8, when a user input to rotate the viewer tool 610 is received, the medical image display apparatus 200 may display by changing the angle of the viewer tool 610.

Figure 9:
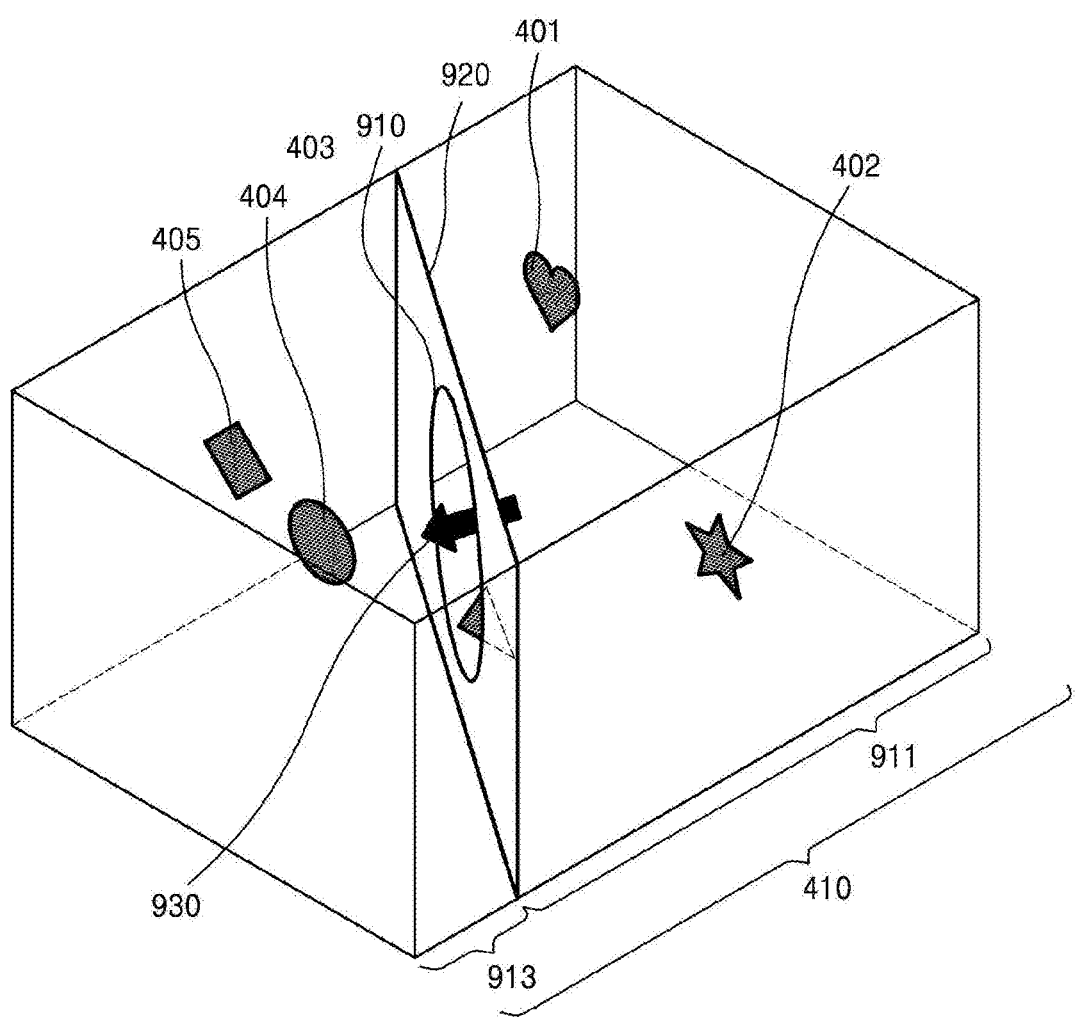

As illustrated in FIG. 9, when at least one of the position, angle, size, and shape of the viewer tool 610 is changed, the medical image display apparatus 200 may determine a section 920 of FIG. 9 determined based on the viewer tool 610, as the second section of the object. The medical image display apparatus 200 may determine the second section 920 of the object based on the change in the position, angle, size, and shape of the viewer tool 610.

The medical image display apparatus 200 may determine the second direction to render the volume data 410 based on the viewer tool 610. For example, as illustrated in FIG. 9, the medical image display apparatus 200 may determine a direction perpendicular to the second section 920, as the second direction. The second direction is indicated by an arrow 930.

The medical image display apparatus 200 may generate the second image by rendering the volume data 410 in the second direction based on the second section 920.

For example, the medical image display apparatus 200 may generate the second image by dividing the volume data 410 into two pieces of sub-volume data 911 and 913 based on the second section 920 and rendering one of the two sub-volume data 911 and 913, that is, the sub-volume data 913, in the second direction. For example, the second direction is perpendicular to the second section and may be determined based on direction information included in the viewer tool 610.

The medical image display apparatus 200 may select at least a partial area of the second image on the first image 510 based on the position, size, and shape of the viewer tool 610. The medical image display apparatus 200 may display a selected partial area on the screen.

Figure 10:
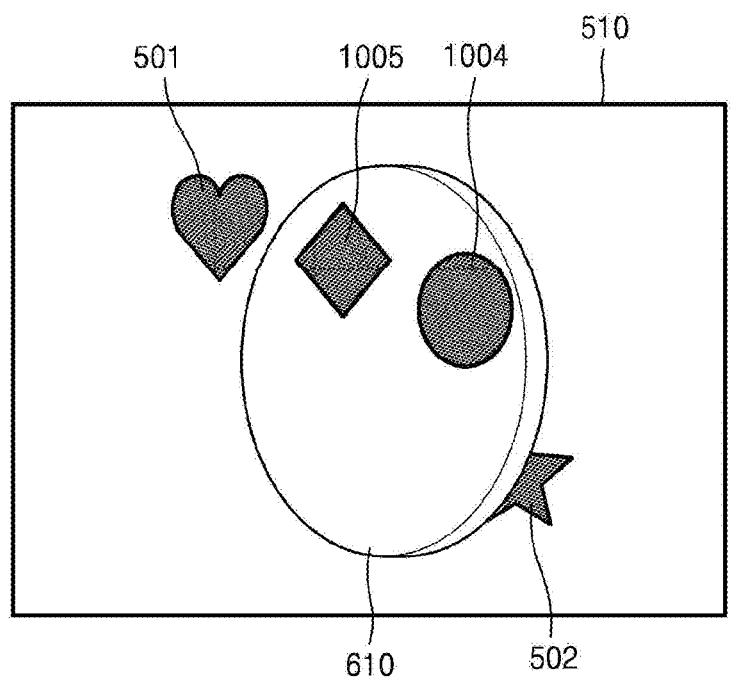

As illustrated in FIG. 10, the second image may be displayed on the viewer tool 610. The second image of FIG. 10 includes images 1004 and 1005 that represent the tissues 404 and 405 included in the sub-volume data 913, corresponding to the position, size, and shape of the viewer tool 610.

As illustrated in FIGS. 8 and 10, the medical image display apparatus 200 may generate and display different second images by determining different sections 420 and 920 of the object based on the angle of the viewer tool 610 and rendering the volume data 410 based on the different sections. For example, the angle of the viewer tool 610 may signify the angle of a section of the object indicated by the viewer tool 610. The medical image display apparatus 200 may display the viewer tool 610 whose shape is changed as the angle of the viewer tool 610 is changed.

FIGS. 8 and 10 illustrate an exemplary embodiment in which the second image is displayed on the viewer tool 610. However, the present exemplary embodiment is not limited thereto, and the medical image display apparatus 200 may separately display the first image 510 and the second image in different areas on the screen or may display the first image 510 and the second image to be partially overlapped with each other.

Figure 11:
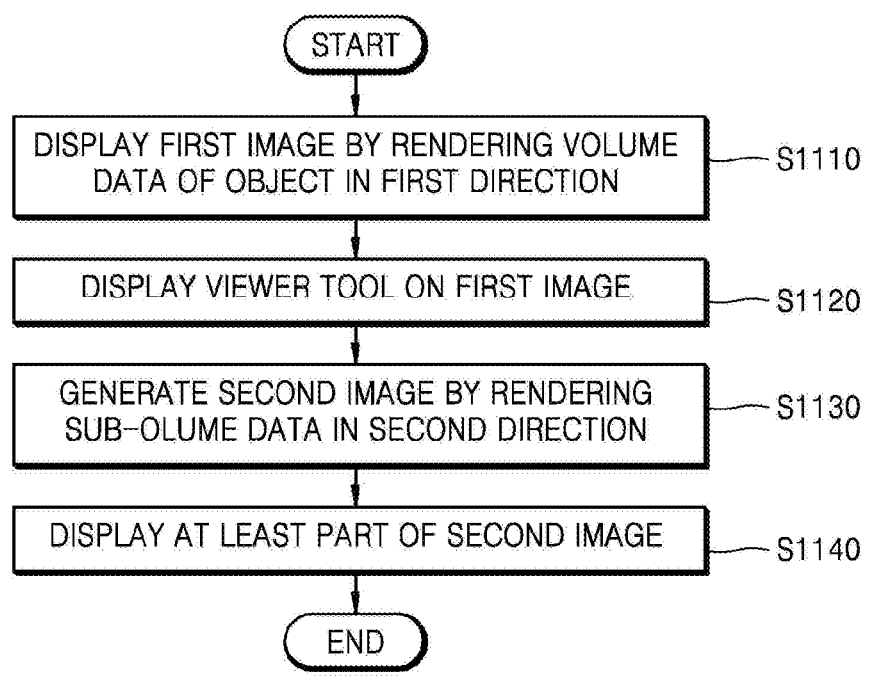
FIG. 11 is a flowchart for explaining a method of displaying a medical image by an apparatus for displaying a medical image, according to an exemplary embodiment.

FIG. 11 is a flowchart for explaining a method of displaying a medical image by an apparatus for displaying a medical image, according to an exemplary embodiment.

Referring to FIG. 11, a method of displaying a medical image according to an exemplary embodiment may include operations processed by the medical image display apparatus 200 of FIG. 2. Accordingly, even when omitted in the below descriptions, the descriptions presented above regarding the medical image display apparatus 200 of FIG. 2 may be applied to the method of displaying a medical image of FIG. 11.

In S1110, the medical image display apparatus 200 may display the first image generated by rendering the volume data of the object in the first direction.

The medical image display apparatus 200 may divide the volume data into two pieces of sub-volume data based on the first section of the object. The medical image display apparatus 200 may generate the first image by rendering one of the two sub-volume data in the first direction. The first image may be perpendicular to the first section.

In S1120, the medical image display apparatus 200 may display the viewer tool on the first image. The viewer tool may be displayed on the first image to generate the second image rendered in the second direction that is different from the first direction.

The viewer tool may include the direction information indicating the second direction to render the volume data. The viewer tool may show the second section of the object to determine the two sub-volume data as the medical image display apparatus 200 divides the volume data. The viewer tool may show the second direction to render one of the two sub-volume data to generate the second image.

The medical image display apparatus 200 may further display the viewer tool and the viewing angel information about the range of the object displayed on the second image that is generated based on the viewer tool.

In S1130, the medical image display apparatus 200 may generate the second image by rendering the sub-volume data included in the volume data in the second direction shown by the viewer tool.

First, the medical image display apparatus 200 may determine the second direction based on the viewer tool. For example, the medical image display apparatus 200 may determine the second direction based on at least one of the position, angle, and shape of the viewer tool.

The medical image display apparatus 200 may determine the second section of the object based on at least one of the position and shape of the viewer tool displayed on the first image. The second section may be the same section as the first section or a section crossing the first section. The medical image display apparatus 200 may determine one of the two directions perpendicular to the second section, as the second direction, based on the direction information of the viewer tool. For example, when the second section is the same section as the first section, the medical image display apparatus 200 may determine a direction opposite to the first direction as the second direction.

Next, the medical image display apparatus 200 may generate the second image by rendering the volume data in the determined second direction.

The medical image display apparatus 200 may generate the second image by dividing the volume data into two pieces of sub-volume data based on the second section and rendering one of the two sub-volume data in the second direction.

The medical image display apparatus 200 may generate the second image by rendering the sub-volume data included in the volume data in the second direction indicated by the viewer tool based on the viewing angle information. The medical image display apparatus 200 may generate the second image representing a spatial area of the inside of the object determined based on the viewing angle information changed by the user input.

The medical image display apparatus 200 may generate the second image by rendering the volume data using a rendering parameter that is different from the rendering parameter applied to the first image.

In S1140, the medical image display apparatus 200 may display at least a part of the second image.

The medical image display apparatus 200 may separately display the first image and the second image in different areas on the screen. Alternatively, the medical image display apparatus 200 may display the first image and the second image in one area so that the second image is displayed overlapping the first image. For example, the medical image display apparatus 200 may display the second image on the viewer tool.

Also, the medical image display apparatus 200 may further include receiving a user input to change at least one of the position, angle, size, and shape of the viewer tool. The medical image display apparatus 200 may generate the third image by rendering the volume data based on the viewer tool in which at least one of the position, angle, size, and shape is changed. The medical image display apparatus 200 may display the third image instead of the second image.

As described above, the medical image display apparatus 200 according to the present exemplary embodiment may enable the user to observe the ROI at various angles based on the viewer tool. Also, the medical image display apparatus 200 according to the present exemplary embodiment may enable the user to observe the ROI simultaneously at various angles, by displaying, on a single screen, 3D images rendered in a plurality of directions with respect to the ROI of the object.

Also, the medical image display apparatus 200 according to the present exemplary embodiment may generate an image of the ROI by rendering the volume data in a predetermined rendering method. Accordingly, according to the present exemplary embodiment, the image of the ROI is highlighted so as to be distinguished from the other images.

Also, the medical image display apparatus 200 according to the present exemplary embodiment may display on a single screen a main image generated by rendering the volume data in a predetermined direction and a sub-image generated by rendering the volume data in a direction opposite to a predetermined direction. Accordingly, according to the present exemplary embodiment, the user may easily compare the main image and the sub-image while simultaneously observing the same section of interest in different directions.

Figure 12:
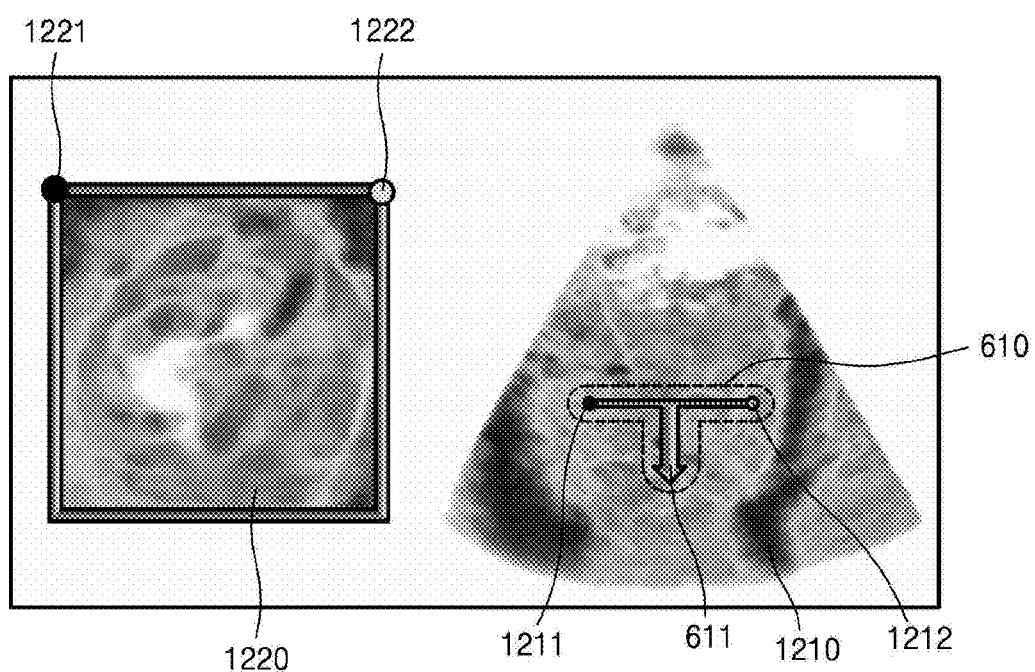
FIG. 12 illustrates an example of an image displayed by the apparatus for displaying a medical image according to an exemplary embodiment.

FIG. 12 illustrates an example of an image displayed by the apparatus for displaying a medical image according to an exemplary embodiment.

As illustrated in FIG. 12, the medical image display apparatus 200 may display a first image 1210 that is generated by rendering the volume data in the first direction.

The medical image display apparatus 200 may display the viewer tool 610 on the first image 1210. The viewer tool 610 may display an arrow 611 as the direction information. FIGS. 12 to 20 illustrate the viewer tool 610 that is rectangular. However, the present exemplary embodiment is not limited thereto and the viewer tool 610 may have a variety of shapes such as a circle, an oval, a polygon, etc.

The medical image display apparatus 200 may generate a second image 1220 by determining the second direction based on the viewer tool 610 and rendering the volume data in the second direction. The medical image display apparatus 200 may determine the second section of the object based on the position and shape of the viewer tool 610. In FIG. 12, the medical image display apparatus 200 may generate the second image 1220 based on the second section that is perpendicular to the first section that the first image 1210 represents.

The medical image display apparatus 200 may generate the second image 1220 by rendering the volume data in the direction indicated by the arrow 611 of the viewer tool 610. A point 1221 in the second image of FIG. 12 corresponds to a point 1211 of the viewer tool 610 and a point 1222 in the second image corresponds to a point 1212 of the viewer tool 610. As illustrated in FIG. 12, the medical image display apparatus 200 may display positions corresponding to each other with points in the same color in order to show a correlation between the viewer tool 610 and the second image 1220.

Also, the medical image display apparatus 200 may select at least a partial area of the second image 1220 based on the size and shape of the viewer tool 610 and display only the selected partial area on the screen. In FIG. 12, a rectangular area selected in the second image 1220 is displayed based on the rectangular shape of the viewer tool 610.

Alternatively, the medical image display apparatus 200 according to the present exemplary embodiment may change at least one of the position, angle, size, and shape of the viewer tool 610. The medical image display apparatus 200 may update the second image according to a change in the viewer tool 610, by rendering the volume data based on the viewer tool 610 that is changed according to the user input.

Figure 13A:
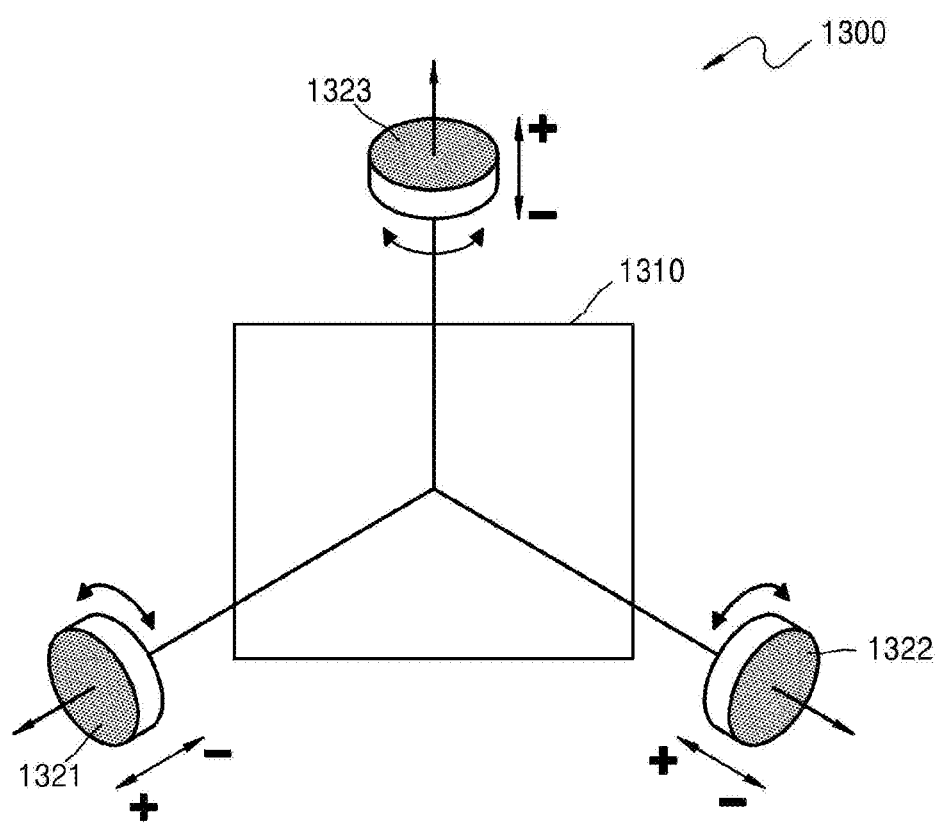
FIG. 13A illustrates an example of a graphical user interface (GUI) for controlling a viewer tool that is displayed on a first image, according to an exemplary embodiment.

FIG. 13A illustrates an example of the GUI for controlling the viewer tool that is displayed on the first image, according to an exemplary embodiment.

As illustrated in FIG. 13A, the medical image display apparatus 200 may change the angle of the viewer tool 610 based on the user input to rotate imaginary wheels 1321, 1322, and 1323 displayed on three imaginary axes. When the angle of the viewer tool 610 is changed by a GUI 1300 illustrated in FIG. 13B, the shape of the viewer tool 610 displayed on the screen may be displayed by being changed. In other words, the medical image display apparatus 200 may change the shape of the viewer tool 610 as if the viewer tool 610 is rotated in a 3D space based on the user input. As the shape of the viewer tool 610 is changed, the medical image display apparatus 200 may change the angle of the second section that is a reference for generating the second image and change the second direction in which the volume data is rendered. In other words, the medical image display apparatus 200 may generate the second image by rendering the volume data based on the second section rotated according to the user input to rotate the imaginary wheels 1321, 1322, and 1323.

Also, the medical image display apparatus 200 may change the position of the viewer tool 610 based on the user input to move the imaginary wheels 1321, 1322, and 1323 along the axes. As the position of the viewer tool 610 is changed, the medical image display apparatus 200 may change the position of the second section that is a reference for generating the second image. Or, as the position of the viewer tool 610 is changed, the medical image display apparatus 200 may change a selection area selected in the second image. The medical image display apparatus 200 may display on the screen the selection area changed in the second image.

According to the present exemplary embodiment, the viewer tool 610 may show a section that divides a spatial area of the object that the volume data represents. The medical image display apparatus 200 may generate the second image by rendering the volumes data based on the second section of the object that the viewer tool 610 indicates. The medical image display apparatus 200 may generate the second image by rendering in the second direction one of two pieces of sub-volume data obtained by dividing the volume data based on the second section.

Figure 13B:
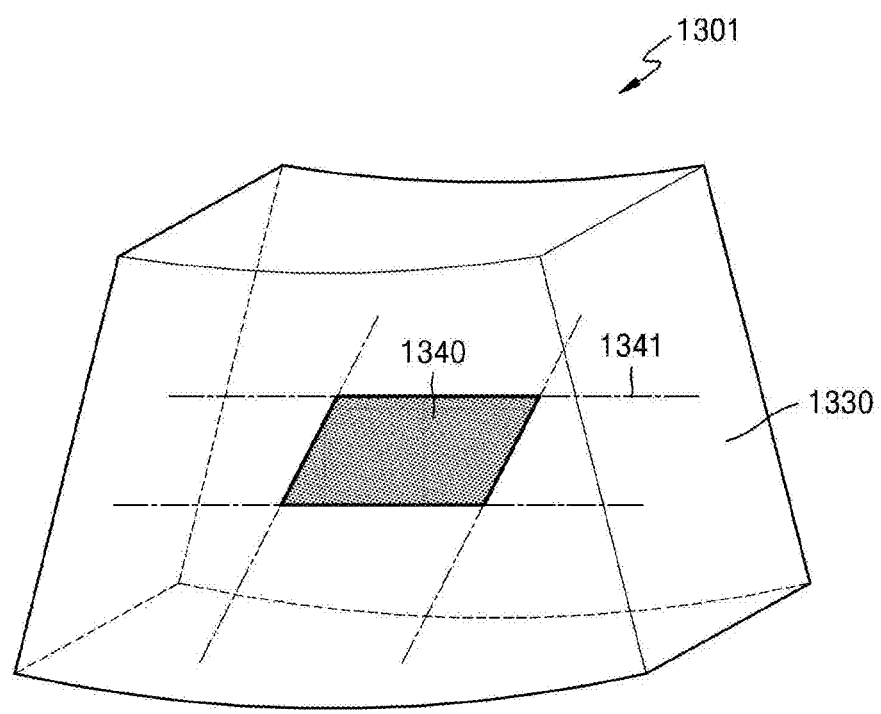
FIG. 13B illustrates an example of a graphical user interface (GUI) for controlling a viewer tool that indicates a section of volume data, according to an exemplary embodiment.

FIG. 13B illustrates an example of the GUI for controlling the viewer tool that indicates a section of the volume data, according to an exemplary embodiment.

As illustrated in FIG. 13B, the medical image display apparatus 200 may provide a GUI 1301 including information about a section in the volume data that the viewer tool 610 indicates. The GUI 1301 may provide information about a relative positional relationship between the section indicated by the viewer tool 610 and the volume data.

The GUI 1301 may include an image 1330 indicating the volume data and an image 1340 indicating a section corresponding to the viewer tool 610. The GUI 1301 may provide information about which section used for dividing the volume data into the sub-volume data the second image generated based on the viewer tool 610 corresponds. The GUI 1301 may include an auxiliary line 1341 that provides information about the position and angle of the section corresponding to the viewer tool 610 in the volume data.

The medical image display apparatus 200 may change at least one of the position, angle, and shape of the viewer tool 610 based on the user input to change at least one of the position, angle, and shape of the image 1340 indicating a section corresponding to the viewer tool 610.

For example, when the angle of the viewer tool 610 is changed by using the image 1340 of FIG. 13B, the shape of the viewer tool 610 and the shape of the image 1340 displayed on the screen may be changed. In other words, the medical image display apparatus 200 may change the shape of the viewer tool 610 as if the viewer tool 610 is rotated in a 3D space based on the user input. As the shape of the viewer tool 610 is changed, the medical image display apparatus 200 may change the angle of the second section that is a reference for generating the second image and change the second direction in which the volume data is rendered. In other words, the medical image display apparatus 200 may generate the second image by rendering the volume data based on the second section that is rotated according to the user' input to rotate the image 1340.

Also, the medical image display apparatus 200 may change the position of the viewer tool 610 based on the user input to move the image 1340. As the position of the viewer tool 610 is changed, the medical image display apparatus 200 may change the position of the second section that is a reference for generating the second image or change a selection area selected in the second image. The medical image display apparatus 200 may display on the screen a changed selection area in the second image.

Figure 14A:
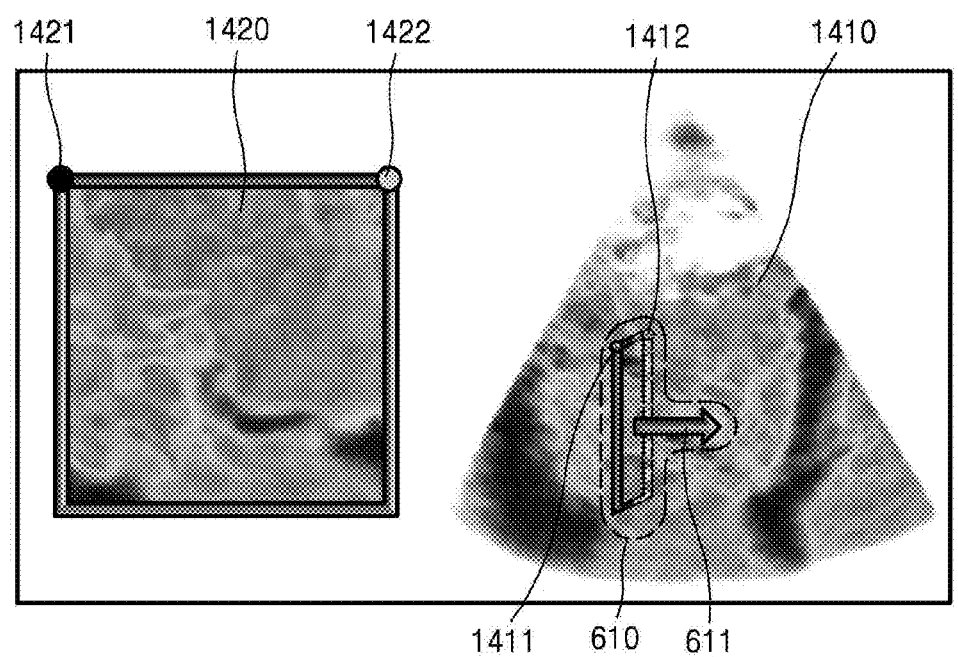
FIGS. 14A and 14B illustrate examples of images displayed by the apparatus for displaying a medical image according to exemplary embodiments.

FIG. 14A illustrates an example of an image displayed by the apparatus for displaying a medical image according to an exemplary embodiment.

As illustrated in FIG. 14A, the medical image display apparatus 200 may display a first image 1410 that is generated by rendering the volume data in the first direction.

The medical image display apparatus 200 may display the viewer tool 610 on the first image 1410. The viewer tool 610 may display the arrow 611 as the direction information. The medical image display apparatus 200 may determine the second direction based on the viewer tool 610 and generate a second image 1420 by rendering the volume data in the second direction. The medical image display apparatus 200 may determine the second section based on the position and shape of the viewer tool 610. In FIG. 14A, the medical image display apparatus 200 may generate the second image 1420 based on the second section crossing the first section that the first image 1410 represents.

The medical image display apparatus 200 may generate the second image 1420 by rendering the volume data in the direction indicated by the arrow 611 of the viewer tool 610. A point 1421 of the second image 1420 of FIG. 14A corresponds to a point 1412 of the viewer tool 610, and a point 1422 of the second image 1420 corresponds to a point 1411 of the viewer tool 610.

Also, the medical image display apparatus 200 may select at least a partial area of the second image 1420 based on the size and shape of the viewer tool 610, and display only a selected partial area on the image. In FIG. 14A, a rectangular area selected in the second image 1420 is displayed based on a rectangular shape of the viewer tool 610.

Figure 14B:
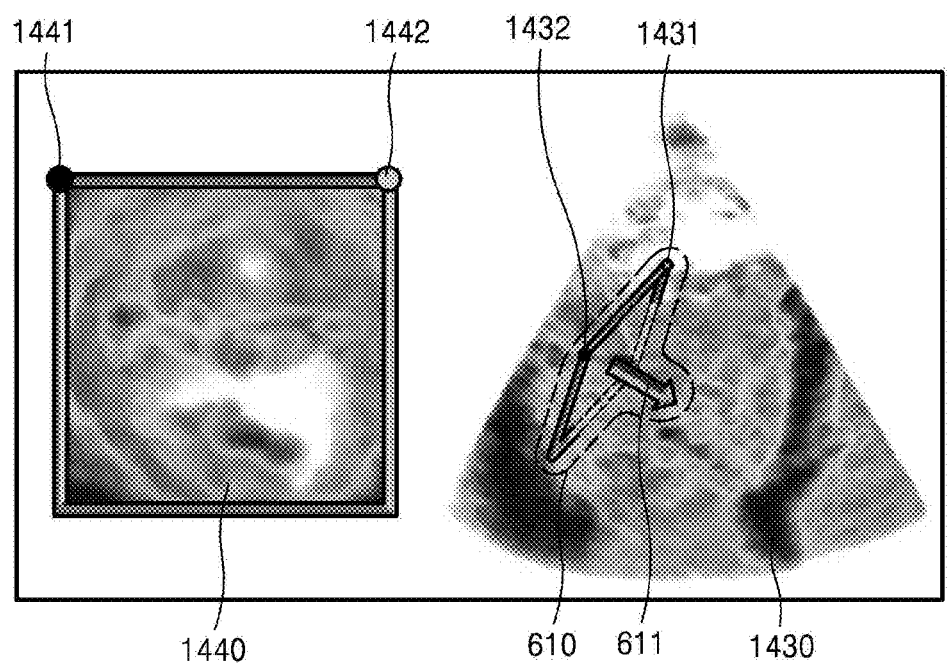

FIG. 14B illustrates an example of an image displayed by the apparatus for displaying a medical image according to an exemplary embodiment.

As illustrated in FIG. 14B, the medical image display apparatus 200 may display a first image 1430 that is generated by rendering the volume data in the first direction.

The medical image display apparatus 200 may display the viewer tool 610 on the first image 1430. The viewer tool 610 may display the arrow 611 as the direction information. The medical image display apparatus 200 may determine the second direction based on the viewer tool 610 and generate a second image 1440 by rendering the volume data in the second direction. The medical image display apparatus 200 may determine the second section based on the position and shape of the viewer tool 610. In FIG. 14B, the medical image display apparatus 200 may generate the second image 1440 based on the second section crossing the first section that the first image 1430 represents.

The medical image display apparatus 200 may generate the second image 1440 by rendering the volume data in the direction indicated by the arrow 611 of the viewer tool 610. A point 1441 of the second image 1440 of FIG. 14B corresponds to a point 1432 of the viewer tool 610, and a point 1442 of the second image 1440 corresponds to a point 1431 of the viewer tool 610.

Also, the medical image display apparatus 200 may select at least a partial area of the second image 1440 based on the size and shape of the viewer tool 610, and display only a selected partial area on the image. In FIG. 14B, a rectangular area selected in the second image 1440 is displayed based on a rectangular shape of the viewer tool 610.

As illustrated in FIGS. 12, 14A, and 14B, the medical image display apparatus 200 may generate and display the second images 1220, 1420, and 1440, which are different from one another, based on the size, position, and shape of the viewer tool 610. Accordingly, according to the present exemplary embodiment, the user may precisely observe a desire portion of the object at various angles by simply adjusting the viewer tool 610.

Alternatively, the medical image display apparatus 200 according to the present exemplary embodiment may change the range of the object, that is, a viewing angle, indicated by the second image generated based on the viewer angle based on the user input.

Figure 15A:
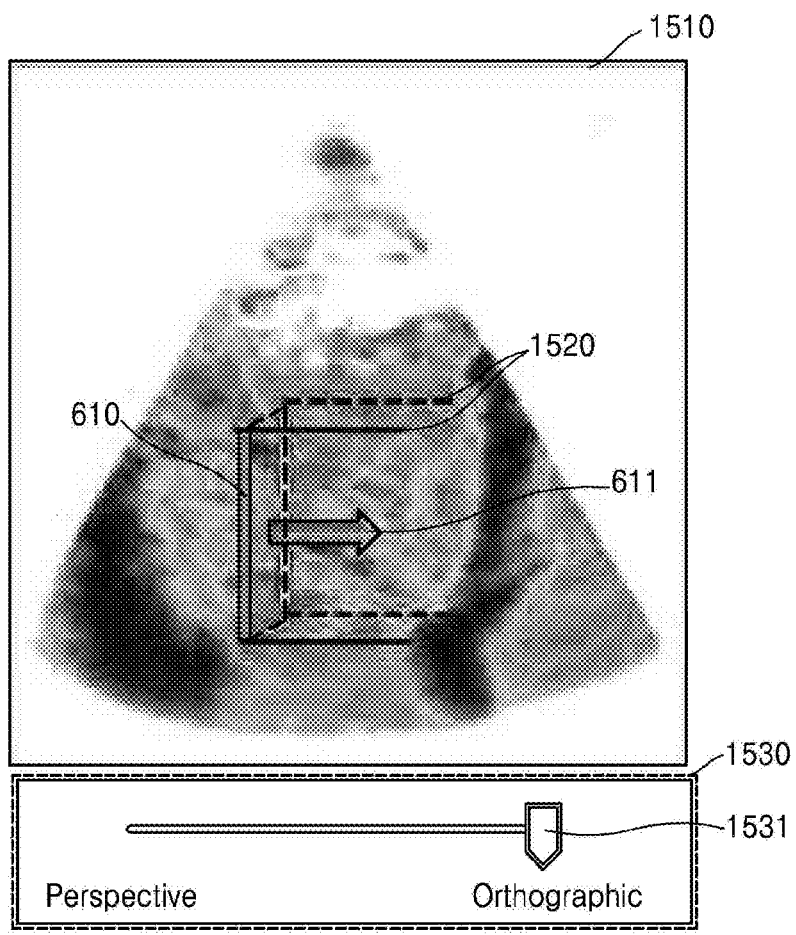
FIGS. 15A and 15B illustrate examples of images displayed by the apparatus for displaying a medical image according to exemplary embodiments.
Figure 15B:
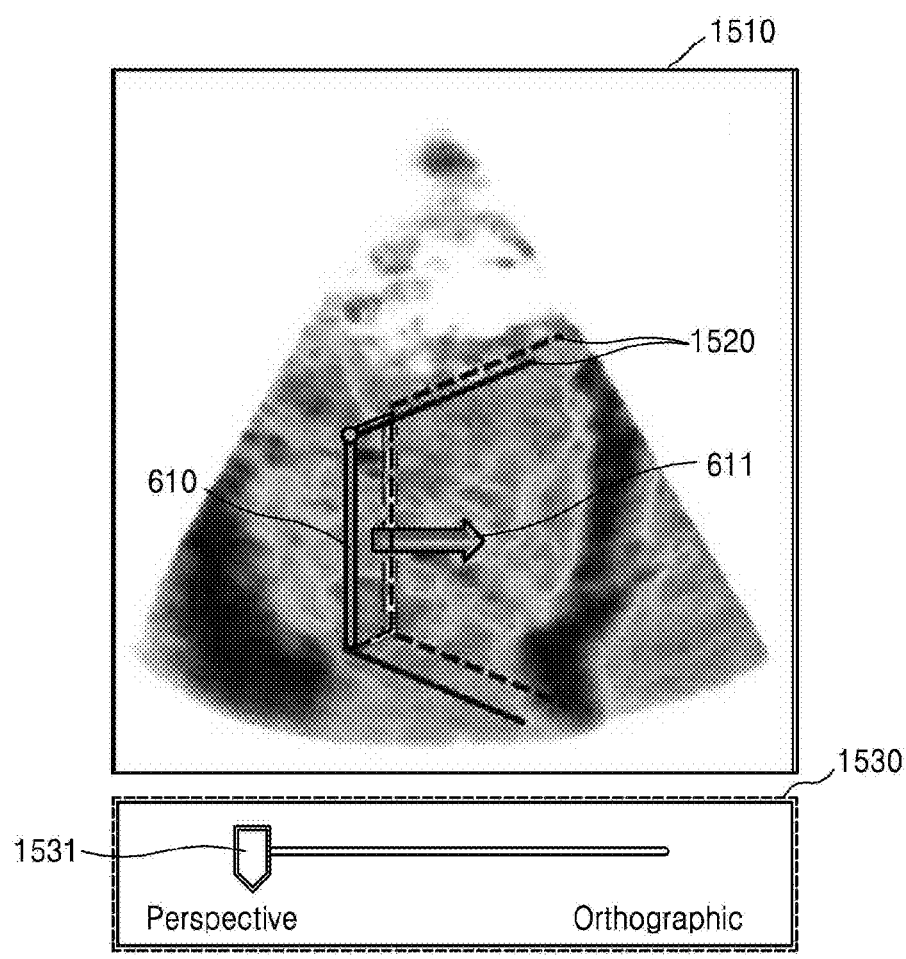

As illustrates in FIGS. 15A and 15B, the medical image display apparatus 200 may provide viewing angle information 1520 indicating a range of the object indicated by the second image generated based on the viewer tool. For example, the medical image display apparatus 200 may render the volume data in an orthographic projection method or a perspective projection method, based on the viewing angle information 1520. An image rendered in the orthographic projection method represents the length of the object to be identical regardless of a distance from a reference surface. In contrast, an image rendered in the perspective projection method represents the size of a part of the object to be greater as a distance from the reference surface decreases, thereby providing depth perception.

Referring to FIG. 15A, the first image 1510, the viewer tool 610, and the viewing angle information 1520 generated by rendering the volume data in the first direction are displayed. The medical image display apparatus 200 may generate the second image by rendering the sub-volume data included in the volume data of the object based on the viewing angle information 1520.

The medical image display apparatus 200 may change the viewing angle information based on the user input. As illustrated in FIGS. 15A and 15B, the medical image display apparatus 200 may provide a GUI 1530 to change the viewing angle information.

The medical image display apparatus 200 may change the viewing angle information that is a range of the object indicated by the second image generated based on the viewer tool 610, based on the user input through the GUI 1530.

As illustrated in FIG. 15B, the medical image display apparatus 200 may change the viewing angle information 1520 based on the user input that moves a slide button 1531 of the GUI 1530 from "Orthographic" to "Perspective". When the medical image display apparatus 200 displays the viewing angle information 1520 of FIG. 15B, the medical image display apparatus 200 may generate the second image indicating a larger spatial area of the object compared to the second image that is generated when the viewing angle information 1520 of FIG. 15A is displayed.

FIGS. 15A and 15B illustrate exemplary embodiments of changing the viewing angle information 1520 based on the user input through the GUI 1530. However, the present exemplary embodiment is not limited to FIGS. 15A and 15B, the medical image display apparatus 200 may change the viewing angle information based on the user input of adjusting the position and angle of the viewing angle information 1520 displayed on the first image 1510.

Alternatively, FIGS. 12, 14A, and 14B illustrate an exemplary case of displaying the first image and the second image in separate screen areas. However, the present exemplary embodiment is not limited thereto, and the first image and the second image may be displayed to be at least partially overlapped with each other. For example, as illustrated in FIG. 16, a second image 1620 may be displayed in the viewer tool 610 displayed on a first image 1610.

Figure 16:
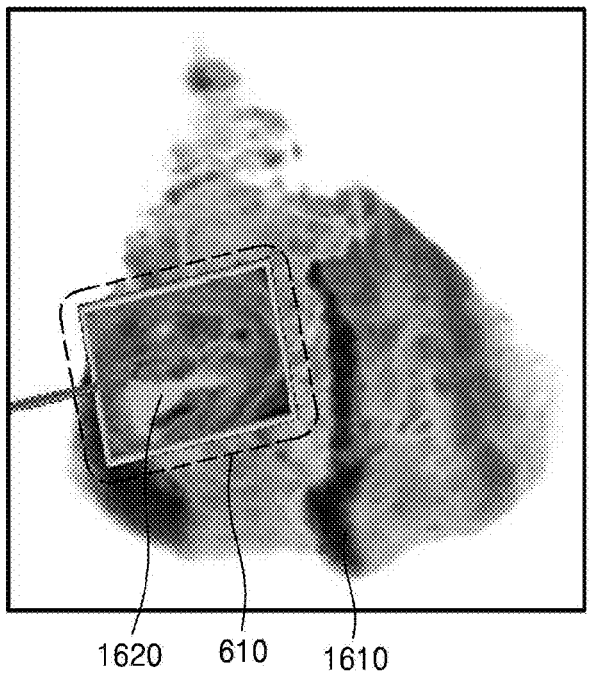
FIG. 16 illustrates an example of an image displaying a second image on the viewer tool according to an exemplary embodiment.

As illustrated in FIG. 16, the medical image display apparatus 200 may provide the viewer tool 610 whose size, position, and shape may be freely adjusted by the user, on the first image 1610 that is a 3D medical image. Accordingly, the user may more precisely observe the ROI at various angles based on the second image 1620 that is displayed by being updated by adjusting the viewer tool 610. For example, the user who uses the medical image display apparatus 200 according to the present exemplary embodiment may receive an image of a valve by using the viewer tool 610 displayed on a 3D apical view image while viewing the 3D apical view image. The medical image display apparatus 200 may display images of valves to be overlapped with the 3D apical view image at positions corresponding to the valves on the 3D apical view image, by displaying a plurality of viewer tools on the 3D apical view image.

Also, according to the present exemplary embodiment, the medical image display apparatus 200 mage generate the second image 1620 by rendering the volume data by using rendering parameters that are different from the rendering parameters applied to the first image 1610. For example, the medical image display apparatus 200 may generate the second image 1620 so that the second image 1620 that is an image of the ROI is highlighted compared to a surrounding area. Accordingly, the medical image display apparatus 200 according to the present exemplary embodiment may enable the user to more intuitively and precisely observe the ROI.

Alternatively, the medical image display apparatus 200 according to the present exemplary embodiment may change the display mode based on the user input.

Figure 17:
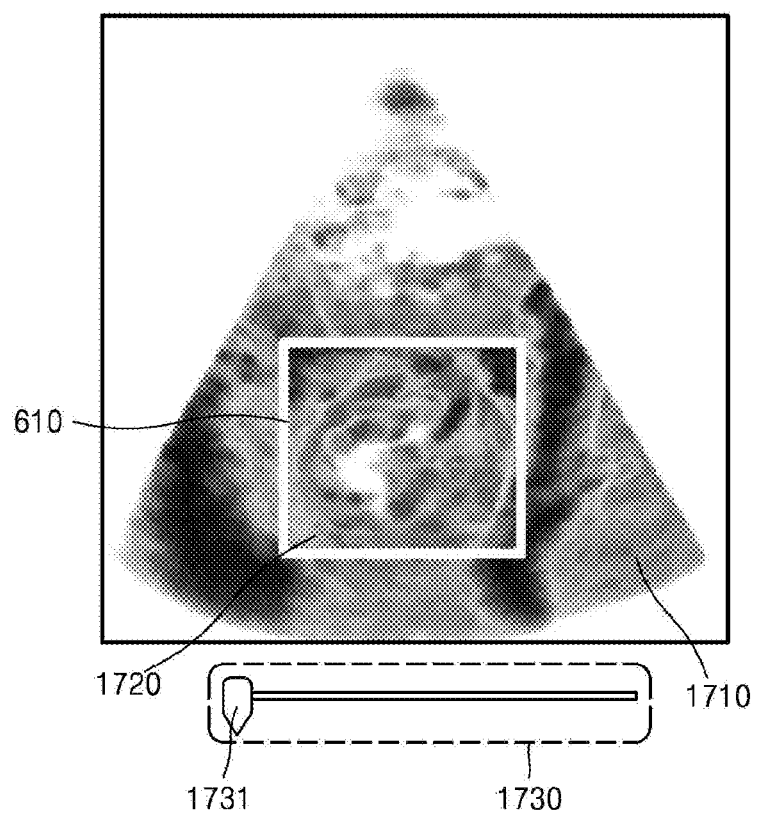
FIGS. 17 and 18 illustrate examples of images provided with a GUI capable of changing a display mode, according to exemplary embodiments.
Figure 18:
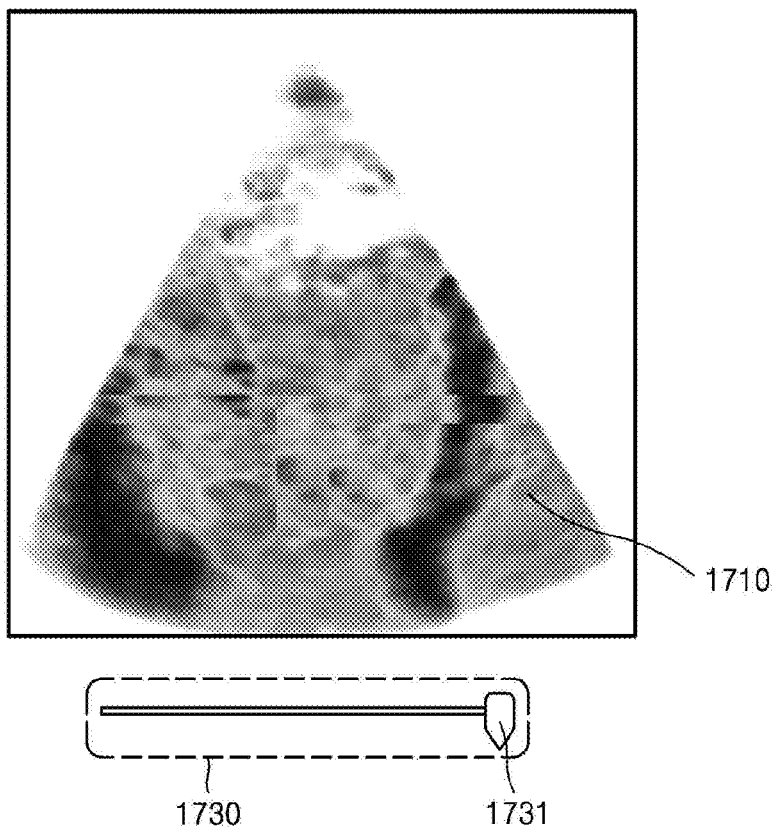

As illustrated in FIGS. 17 and 18, the medical image display apparatus 200 may provide a GUI 1730 to change the display mode.

Referring to FIG. 17, a first image 1710 generated by rendering the volume data in the first direction, the viewer tool 610, and a second image 1720 generated by rendering the volume data in the second direction are displayed. The medical image display apparatus 200 may change the display mode based on the user input through the GUI 1730, so as not to display the viewer tool 610 and the second image 1720. As illustrated in FIG. 18, the medical image display apparatus 200 may change the display mode based on the user input to move a slide button 1731 of the GUI 1730 to the right, so as to display only the first image 1710 without displaying the viewer tool 610 and the second image 1720.

Also, when the slide button 1731 is located in the middle of the GUI 1730, the medical image display apparatus 200 may display the first image 1710 and the second image 1720 by blending the same. For example, the medical image display apparatus 200 may display an image obtained by blending the first image 1710 and the second image 1720, by adjusting transparency of at least one of the first image 1710 and the second image 1720, based on the position of the slide button 1731.

Alternatively, the medical image display apparatus 200 according to the present exemplary embodiment may contract or enlarge a displayed image based on the user input.

Figure 19:
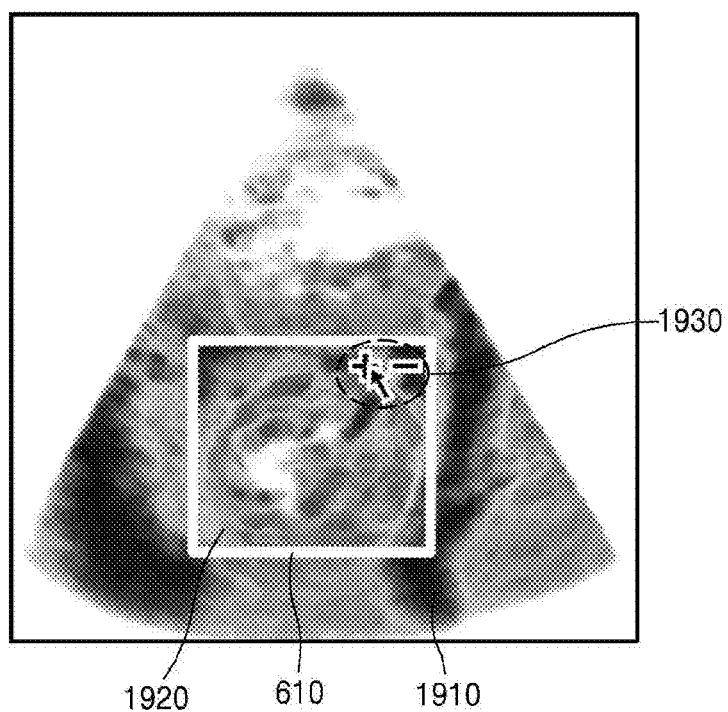
FIGS. 19 and 20 illustrate examples of images provided with a GUI capable of contracting or enlarging the second image, according to exemplary embodiments.
Figure 20:
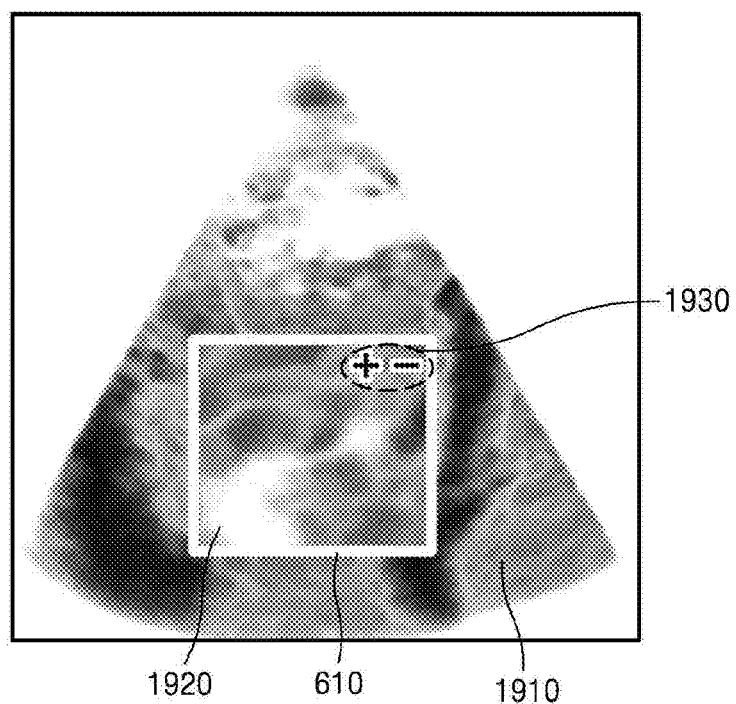

As illustrated in FIGS. 19 and 20, the medical image display apparatus 200 may provide a GUI 1930 to adjust an enlargement ratio of the second image.

Referring to FIG. 19, a first image 1910 generated by rendering the volume data in the first direction, the viewer tool 610, and a second image 1920 generated by rendering the volume data in the second direction are displayed. As illustrated in FIG. 19, the medical image display apparatus 200 may display the second image 1920 that is enlarged or contracted based on the user input to select an enlargement button (+) or a contraction button (−) of the GUI 1930. As illustrated in FIG. 19, when a user input to select the "+" button included in the GUI 1930, as illustrated in FIG. 20, the medical image display apparatus 200 may display the second image 1920 that is enlarged.

The medical image display apparatus 200 according to the present exemplary embodiment may be applied to an ultrasound system for generating and displaying an ultrasound image. Accordingly, a method of displaying a medical image according to an exemplary embodiment may be performed by an ultrasound system 2000 illustrated in FIG. 21, and the medical image display apparatus 200 may be included in the ultrasound system 2000 of FIG. 21.

Figure 21:
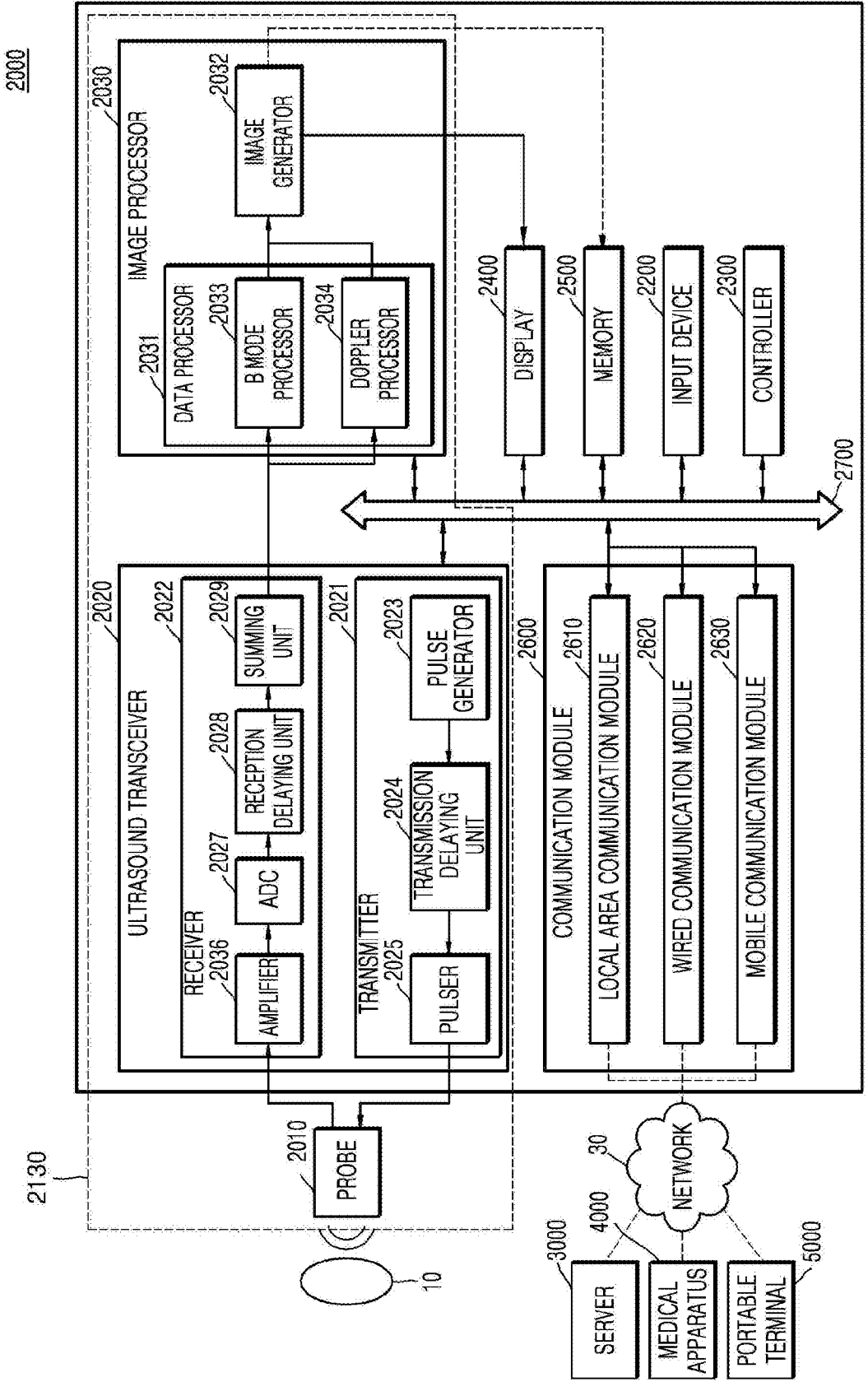
FIG. 21 is a block diagram of an ultrasound system to which the apparatus for displaying a medical image according to an exemplary embodiment is applicable.

For example, the volume data acquirer 210 of FIG. 2 may correspond to a probe 2010 and an ultrasound transceiver 2020 of FIG. 21, and the image processor 220 of FIG. 2 may correspond to an image processor 2030 of FIG. 21. The display 230 of FIG. 2 may correspond to a display 2400 of FIG. 21, and the controller 240 of FIG. 2 may correspond to a controller 2300 of FIG. 21. According to the present exemplary embodiment, when the volume data acquirer 210 acquires the volume data from an external device or server instead of directly forming the volume data, the volume data acquirer 210 of FIG. 2 may correspond to a communication unit 2600 or a memory 2500 of FIG. 21.

Also, the probe 211 of FIG. 3 may correspond to the probe 2010 of FIG. 21, and the ultrasound transceiver 213 of FIG. 3 may correspond to the ultrasound transceiver 2020 of FIG. 21. Also, the user input unit 250 of FIG. 3 may correspond to a user input unit 2200 of FIG. 21, and the communication unit 260 of FIG. 3 may correspond to the communication unit 2600 of FIG. 21. The memory 270 of FIG. 3 may correspond to the memory 2500 of FIG. 21. When one structure corresponds to another structure, the latter structure may perform a part or whole of the function performed by the former structure.

The respective elements included in the ultrasound system 2000 of FIG. 21 are described below in detail.

According to the present exemplary embodiment, the probe 2010, the ultrasound transceiver 2020, and the image processor 2030 may acquire ultrasound image data about an object 20. According to the present exemplary embodiment, the ultrasound image data may be 2D ultrasound image data or 3D ultrasound image data about the object 20.

According to the present exemplary embodiment, a transmitter 2021 included in the ultrasound transceiver 2020 may include a pulse generator 2023, a transmission delaying unit 2024, and a pulser 2025, as illustrated in FIG. 21.

The transmitter 2021 may supply a driving signal to the probe 2010. The pulse generator 2023 generates a pulse to form a transmission ultrasound wave according to a predetermined pulse repetition frequency (PRF). The transmission delaying unit 2024 applies to the pulse a delay time to determine transmission directionality. Each pulse to which the delay time is applied corresponds to each of a plurality of piezoelectric vibrators included in the probe 2010. The pulser 2025 applies the driving signal, or a driving pulse, to the probe 2010 at a timing corresponding to each pulse to which the delay time is applied.

According to the present exemplary embodiment, a receiver 2022 included in the ultrasound transceiver 2020 may include an amplifier 2026, an analog-to-digital converter (ADC) 2027, a reception delaying unit 2028, and a summing unit 2029, as illustrated in FIG. 21.

The receiver 2022 may generate ultrasound data by processing a response signal received from the probe 2010. The amplifier 2026 amplifies the response signal for each channel. The ADC 2027 performs analog-to-digital conversion on the amplified response signal. The reception delaying unit 2028 applies a delay time to determine reception directionality to the digitally converted response signal. The summing unit 2029 sums the response signal processed by the reception delaying unit 2028, thereby generating ultrasound image data.

According to the present exemplary embodiment, the probe 2010 may include a part of whole of elements included in the transmitter 2021 and the receiver 2022 of FIG. 21 and may perform a part or whole of the function performed by the transmitter 2021 and the receiver 2022.

The image processor 2030 generates an ultrasound image through a scan conversion process on the ultrasound image data generated by the ultrasound transceiver 2020. Alternatively, the ultrasound image may include not only a gray scale image obtained by scanning the object in an amplitude mode "A mode", a brightness mode "B mode", and a motion mode "M mode", but also a Doppler image representing a moving object by using a Doppler effect. The Doppler image may include a blood flow Doppler image indicating a flow of blood, which is referred to as a color Doppler image, a tissue Doppler image indicating a movement of a tissue, and a spectral Doppler image indicating a movement velocity of the object as a waveform.

A B-mode processor 2033 processes the ultrasound image data by extracting a B mode component from the ultrasound image data. An image generator 2032 may generate an ultrasound image in which strength of a signal is presented in brightness based on the M mode component extracted by the B-mode processor 2033.

The image processor 2030 may include an elasticity processor (not shown). An elasticity processor (not shown) processes elasticity data by extracting a velocity component of a shear wave, for example, a shear ware coefficient, from the elasticity data. The image generator 2032 may generate an elasticity image in which the velocity of a shear wave is represented in color, based on the velocity component of a shear wave, for example, a shear ware coefficient, extracted by the elasticity processor.

Also, a Doppler processor 2034 may extract a Doppler component from the ultrasound image data. The image generator 2032 may generate a Doppler image in which a movement of the object is represented in color or waveform based on the extracted Doppler component.

The image generator 2032 according to the present exemplary embodiment may generate a 3D ultrasound image through a volume rendering process on the volume data, and generate an elasticity image that images a degree of deformation of the object 20 according to pressure.

Furthermore, the image generator 2032 may provide various pieces of additional information in text or graphics on the ultrasound image. For example, the image generator 2032 may add at least one of annotations related to a part or whole of the ultrasound image to the ultrasound image. In other words, the image generator 2032 may analyze the ultrasound image and recommend at least one of annotations related to a part or whole of the ultrasound image based on a result of the analysis. Also, the image generator 2032 may add additional information corresponding to the ROI selected by the user to the ultrasound image.

Alternatively, the image processor 2030 may extract the ROI from the ultrasound image by using an image processing algorithm. For example, the image processor 2030 may extract the ROI from the elasticity image based on the shear wave coefficient. The image processor 2030 may add a color to the ROI, or a pattern or edge thereto.

The user input unit 2700 may signify a device used by a user, for example, a sonographer, to input data to control the ultrasound system 2000. For example, the user input unit 2700 may include a key pad, a dome switch, a touch pad such as a capacitive overlap method, a resistive overlay method, an infrared beam method, a surface acoustic wave method, an integral strain gauge method, or a piezoelectric method, a trackball, a jog switch, etc., but not limited thereto. For example, the user input unit 2700 may further include various input devices such as an electrocardiogram measurement module, a respiration measurement module, a voice recognition sensor, a gesture recognition sensor, a fingerprint recognition sensor, an iris recognition sensor, a depth sensor, a distance sensor, etc.

According to the present exemplary embodiment, the user input unit 2700 may sense not only a real-touch but also a proximity touch. The user input unit 2700 may sense a touch input, for example, touch and hold, tap, double tap, flick, etc., with respect to the ultrasound image. Also, the user input unit 2700 may sense a drag input from a position where a touch input is sensed. Alternatively, the user input unit 2700 may sense multiple touch inputs, for example, pinch, with respect to at least two positions on the ultrasound image.

According to the present exemplary embodiment, the user input unit 2700 may receive an input of interest elasticity information from the user. For example, the user input unit 2700 may receive a range of a shear wave coefficient as the interest elasticity information. The user input unit 2700 may receive inputs of a center shear wave coefficient and an application range as the interest elasticity information. The user input unit 2700 may receive a selection of an interest elasticity range from an elasticity range list including a plurality of elasticity ranges.

According to the present exemplary embodiment, the user input unit 2700 may receive information about a size of interest from the user. The user input unit 2700 may receive a request for deleting a boundary line of at least one of a plurality of tumor of interests corresponding to the interest elasticity information. According to the present exemplary embodiment, the user input unit 2700 may receive an input to change the interest elasticity information.

The controller 2300 controls an overall operation of the ultrasound system 2000. For example, the controller 2300 may generally control the probe 2010, the ultrasound transceiver 2020, the image processor 2030, the user input unit 2700, the display 2400, the memory 2500, and the communication unit 2600.

The display 2400 displays and outputs the information processed by the ultrasound system 2000. For example, the display 2400 may display the ultrasound image, or an UI or GUI related to a control panel (not shown).

The display 2400 may display the elasticity image acquired by using a shear wave. The display 2400 may display the elasticity image by overlapping the elasticity image on the B mode image. The display 2400 may display a tumor of interest in the elasticity image. For example, the display 2400 may display a boundary line on the tumor of interest. The display 2400 may provide measurement information about measurement of a tumor of interest. When a plurality of tumors of interest are detected, the display 2400 may provide the measurement information corresponding to each of the tumors of interest.

When the display 2400 and a touch pad in a layer structure form a touch image, the display 2400 may be used as an input device in addition to an output device. The display 2400 may include at least one of a liquid crystal display, a thin film transistor-liquid crystal display, an organic light-emitting diode, a flexible display, a 3D display, and an electrophoretic display. The ultrasound system 2000 may include two or more displays 2400 according to an embodiment type of the ultrasound system 2000.

The memory 2500 may store a program for processing the controller and store input/output data, for example, ultrasound image data, elasticity data, interest elasticity information, elasticity range list, examinee information, probe information, body marker, additional information, etc.

The memory 2500 may include a storage medium of at least one type of a flash memory type, a hard disk type, a multimedia card micro type, a card type memory, for example, SD or XD memory, random access memory (RAM) static random access memory (SRAM), read-only memory (ROM), electrically erasable programmable ROM (EEPROM), programmable ROM (PROM), magnetic memory, a magnetic disc, an optical disc, etc. Also, the ultrasound system 2000 may run a web storage or a cloud server that performs a storing function of the memory 2500 on the Internet.

The communication unit 2600 may include one or more elements that enable communication between the ultrasound system 2000 and a server 3000, between the ultrasound system 2000 and a medical apparatus 4000, and between the ultrasound system 2000 and a mobile terminal 5000. For example, the communication unit 2600 may include a short-range communication module 2610, a wired communication module 2620, a mobile communication module 2630, etc.

The short-range communication module 2610 refers to a module for short-range communication within a predetermined distance. Short-range communication technology may include Wi-Fi, Bluetooth, BLE, ultra-wideband (UWB), ZigBee, near field communication (NFC), Wi-Fi direct (WFD), infrared data association (IrDA), etc.

The wired communication module 2620 refers to a module for communication using an electric signal or optical signal. Wired communication technology according to an exemplary embodiment may include a pair cable, a coaxial cable, a fiber optic cable, an Ethernet cable, etc.

The mobile communication module 2630 transceives a wireless signal with respect to at least one of a base station, the external devices 4000 and 5000, and the server 3000. The wireless signal may include a voice call signal, a video call signal, or various types of data according to text/multimedia message transceiving.

The communication unit 2600 is connected to a network 30 in a wired or wireless manner and communicates with the external device, for example, the medical apparatus 4000 or the mobile terminal 5000, or with the server 3000. The communication unit 2600 may exchange data with a hospital server or other medical apparatuses in a hospital connected through the Picture Archiving and Communication System (PACS). Also, the communication unit 2600 may communicate data according to the Digital Imaging and Communications in Medicine (DICOM) Standard.

The communication unit 2600 may transceive data related to diagnosis of the object 20, for example, ultrasound image, ultrasound image data, Doppler image data of the object 20, or a medical image imaged by other medical apparatus such as CT, MRI, X-ray, etc., via the network 30. Furthermore, the communication unit 2600 may receive information such as a diagnosis history or treatment schedule of a patient, from the server 3000.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, etc. The computer readable recording medium can also be distributed over network coupled computer systems so that the computer readable code is stored and executed in a distributed fashion.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of displaying a medical image, the method comprising:
   displaying a first three-dimensional (3D) image that is generated by rendering a first volume data of an object in a first direction;
   displaying on the first 3D image, a viewer tool which is a graphic interface image including a plane image, the viewer tool specifying a second volume data to be rendered from among the first volume data for a second 3D image and a second direction in which the second volume data is to be rendered for the second 3D image;
   receiving a user input of moving the viewer tool three-dimensionally on the first 3D image;
   in response to receiving the user input of moving the viewer tool, displaying the moved viewer tool on the first 3D image;
   determining one of two pieces of sub-volume data specified by the plane image included in the moved viewer tool as the second volume data, from among the first volume data, and a direction perpendicular to a section specified by the plane image included in the moved viewer tool as the second direction;
   generating the second 3D image by rendering the determined second volume data in the determined second direction; and
   displaying at least a part of the second 3D image.

2. The method of claim 1, wherein the generating of the second 3D image comprises determining the second direction perpendicular to the section specified by the plane image based on at least one of a position, an angle, and a shape of the viewer tool displayed on the first 3D image.

3. The method of claim 1, wherein the generating of the second 3D image comprises
   determining one of two directions perpendicular to the section specified by the plane image as the second direction.

4. The method of claim 1, wherein the displaying of the viewer tool comprises displaying viewing angle information indicating a range of the object represented by the second 3D image that is generated based on the viewer tool, and
   the generating of the second 3D image comprises:
   generating the second 3D image by rendering the second volume data included in the first volume data in the second direction indicated by the viewer tool based on the viewing angle information.

5. The method of claim 4, wherein the viewer tool comprises direction information indicating which one of two directions that are perpendicular to the section specified by the plane image indicated by the viewer tool is the second direction.

6. The method of claim 1, wherein the first 3D image is generated by rendering in the first direction one of two pieces of sub-volume data obtained by dividing the first volume data based on a first section of the object, and the second 3D image is generated by rendering in the second direction one of two pieces of sub-volume data obtained by dividing the first volume data based on the section specified by the plane image included in the viewer tool, wherein the section specified by the plane image crosses the first section.

7. The method of claim 1, wherein the first 3D image is generated by rendering in the first direction one of two pieces of sub-volume data obtained by dividing the first volume data based on the section specified by the plane image included in the viewer tool, and the second 3D image is generated by rendering in the second direction the other one of the two pieces of sub-volume data obtained by dividing the first volume data, wherein the second direction is opposite to the first direction.

8. The method of claim 1, wherein the second 3D image is generated by rendering the second volume data with a rendering parameter that is different from a rendering parameter applied to the first 3D image.

9. The method of claim 1, further comprising enlarging or contracting the second 3D image based on a user input.

10. An apparatus for displaying a medical image, the apparatus comprising:
    at least one processor generating a first three-dimensional (3D) image by rendering a first volume data of an object in a first direction; and
    a display displaying the first 3D image and displaying, on the first 3D image, a viewer tool which is a graphic interface image, the viewer tool including a plane image which specifies a second volume data to rendered from among the first volume data for a second 3D image and a second direction for the second 3D image,
    a user input unit receiving a user input of moving the viewer tool three-dimensionally on the first 3D image;
    wherein the display, in response to receiving the user input of moving the viewer tool, display the moved viewer tool on the first 3D image,
    wherein the at least one processor determines one of two pieces of sub-volume data specified by the plane image included in the moved viewer tool as the second volume data, from among the first volume data, and a direction perpendicular to a section specified by the plane image included in the moved viewer tool as the second direction,
    wherein the at least one processor generates the second 3D image by rendering the determined second volume data in the determined second direction, and
    wherein the display displays at least a part of the second 3D image.

11. The apparatus of claim 10, wherein the second direction perpendicular to the section specified by the plane image is determined based on at least one of a position, an angle, and a shape of the viewer tool displayed on the first 3D image.

12. The apparatus of claim 10, wherein the second direction is one of two directions perpendicular to the section specified by the plane image.

13. The apparatus of claim 10, wherein the display further displays viewing angle information indicating a range of the object represented by the second 3D image that is generated based on the viewer tool,
    the at least one processor generates the second 3D image by rendering the second volume data included in the first volume data in the second direction indicated by the viewer tool based on the viewing angle information.

14. The apparatus of claim 13, wherein the viewer tool comprises direction information indicating which one of two directions that are perpendicular to the section specified by the plane image indicated by the viewer tool is the second direction.

15. The apparatus of claim 10, wherein the first 3D image is generated by rendering in the first direction one of two pieces of sub-volume data obtained by dividing the first volume data based on a first section of the object, and the second 3D image is generated by rendering in the second direction one of two pieces of sub-volume data obtained by dividing the first volume data based on the section specified by the plane image included in the viewer tool, wherein the section specified by the plane image crosses the first section.

16. The apparatus of claim 10, wherein the first 3D image is generated by rendering in the first direction one of two pieces of sub-volume data obtained by dividing the first volume data based on the section specified by the plane image included in the viewer tool, and the second 3D image is generated by rendering in the second direction the other one of the two pieces of sub-volume data obtained by dividing the first volume data, wherein the second direction being opposite to the first direction.

17. The apparatus of claim 10, wherein the second 3D image is generated by rendering the second volume data with a rendering parameter that is different from a rendering parameter applied to the first 3D image.

18. The apparatus of claim 10, wherein the user input unit receives a user input, wherein the display displays the second 3D image which is enlarged or contracted based on the user input.

19. A non-transitory computer-readable storage medium having stored thereon a program, which when executed by a computer, performs a method for display a medical image, wherein the method comprises:
  displaying a first three-dimensional (3D) image that is generated by rendering a first volume data of an object in a first direction;
  displaying, on the first 3D image, a viewer tool which is a graphic interface image including a plane image, the viewer tool specifying a second volume data to be rendered from among the first volume data for a second 3D image and a second direction in which the second volume data is to be rendered for the second 3D image;
  receiving a user input of moving the viewer tool three-dimensionally on the first 3D image;
  in response to receiving the user input of moving the viewer tool, displaying the moved viewer tool on the first 3D image;
  determining one of two pieces of sub-volume data specified by the plane image included in the moved viewer tool as the second volume data, from among the first volume data, and a direction perpendicular to a section specified by the plane image included in the moved viewer tool as the second direction;
  generating the second 3D image by rendering the determined second volume data in the determined second direction; and
  displaying at least a part of the second 3D image.

20. The method of claim 1, wherein the displaying of the at least a part of the second 3D image comprises displaying the at least a part of the second 3D image on the plane image included in the viewer tool.

21. The method of claim 1, wherein the receiving of the user input of moving the viewer tool three-dimensionally comprises receiving a user input of changing a three dimensional position of the viewer tool or receiving a user input of rotating the viewer tool three-dimensionally.

* * * * *